US009693990B2

(12) United States Patent
Perlman

(10) Patent No.: US 9,693,990 B2
(45) Date of Patent: Jul. 4, 2017

(54) USE OF RHODAMINE DYES TO REDUCE ALVEOLAR SURFACE TENSION

(71) Applicant: THE TRUSTEES OF THE STEVENS INSTITUTE OF TECHNOLOGY, Hoboken, NJ (US)

(72) Inventor: Carrie E. Perlman, New York, NY (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 14/940,675

(22) Filed: Nov. 13, 2015

(65) Prior Publication Data

US 2016/0067210 A1 Mar. 10, 2016

Related U.S. Application Data

(63) Continuation-in-part of application No. 13/650,759, filed on Oct. 12, 2012.

(60) Provisional application No. 62/079,004, filed on Nov. 13, 2014, provisional application No. 61/547,133, filed on Oct. 14, 2011.

(51) Int. Cl.
*A01N 43/16* (2006.01)
*A61K 31/35* (2006.01)
*A61K 31/352* (2006.01)
*A61K 38/38* (2006.01)
*A61K 9/00* (2006.01)
*A61M 16/20* (2006.01)
*A61M 16/00* (2006.01)

(52) U.S. Cl.
CPC .......... *A61K 31/352* (2013.01); *A61K 9/0082* (2013.01); *A61K 38/38* (2013.01); *A61M 16/0006* (2014.02); *A61M 16/0009* (2014.02); *A61M 16/0096* (2013.01); *A61M 16/203* (2014.02); *A61M 16/204* (2014.02); *A61M 16/205* (2014.02); *A61M 16/209* (2014.02); *A61M 16/0051* (2013.01); *A61M 16/0054* (2013.01); *A61M 2016/0027* (2013.01); *A61M 2202/0488* (2013.01); *A61M 2210/1039* (2013.01)

(58) Field of Classification Search
None
See application file for complete search history.

(56) References Cited

U.S. PATENT DOCUMENTS

| | | | |
|---|---|---|---|
| 4,216,776 | A | 8/1980 | Downie |
| 6,180,142 | B1 | 1/2001 | Taeusch |
| 8,967,144 | B2 | 3/2015 | Lurie |
| 9,504,796 | B2 | 11/2016 | Perlman |
| 2009/0208581 | A1 | 8/2009 | Edwards et al. |
| 2017/0021126 | A1 | 1/2017 | Perlman |

OTHER PUBLICATIONS

Wang, Z. et al., Acylation of Pulmonary Surfactant Protein-C Is Required for Its Optimal Surface Active Interactions with Phospholipids, The Journal of Biological Chemistry, vol. 271, No. 32, (1996), 19104-19109.
Ware, L. et al., The acute respiratory distress syndrome, N Engl J Med, 342: 1334-1349, 2000.
Warr, R. et al., Low molecular weight human pulmonary surfactant protein (SP5): Isolation, characterization, and cDNA and amino acid sequences, Proc Natl Acad Sci USA, vol. 84, (1987), 7915-7919.
Warriner, H. et al., A concentration-dependent mechanism by which serum albumin inactivates replacement lung surfactants, Biophys J, 82: 835-842, 2002.
Weg, J. et al., Safety and potential efficacy of an aerosolized surfactant in human sepsis-induced adult respiratory distress syndrome, JAMA, 272: 1433-1438, 1994.
Whitsett, J. et al., Hydrophobic Surfactant-Associated Protein in Whole Lung Surfactant and Its Importance for Biophysical Activity in Lung Surfactant Extracts Used for Replacement Therapy, Pediatric Research, vol. 20, No. 5, (1986), 460-467.
Willson, D. et al., Surfactant for Pediatric Acute Lung Injury, Pediatr Clin N Am, 55, (2008), 545-575.
Willson, D. et al., Effect of exogenous surfactant (calfactant) in pediatric acute lung injury: a randomized controlled trial, JAMA, 293: 470-476, 2005.
Wu, Y. et al., Lung ventilation injures areas with discrete alveolar flooding, in a surface tension-dependent fashion, J Appl Physiol, 117: 788-796, 2014.
Yapicioglu, H. et al., The use of surfactant in children with acute respiratory distress syndrome: efficacy in terms of oxygenation, ventilation and mortality, Pulmonary Pharmacology & Therapeutics, 16, (2003), 327-333.
Yu, S. et al., Reconstitution of surfactant activity by using the 6 kDa apoprotein associated with pulmonary surfactant, Biochem J, 236, (1986), 85-89.
Yu, S. et al., Characterization of the small hydrophobic proteins associated with pulmonary surfactant, Biochimica et Biophysica Acta, vol. 921, No. 3, (1987), 437-448.
Yu, S. et al., Role of bovine pulmonary surfactant-associated proteins in the surface-active property of phospholipid mixtures, Biochim Biophys Acta, 1046: 233-241, 1990.
Yu, S. et al., Effect of pulmonary surfactant protein A and neutral lipid on accretion and organization of dipalmitoylphosphatidycholine in surface films, Journal of Lipid Research, vol. 37, (1996), 1278-1288.
Zasadzinski, J. et al., Inhibition of pulmonary surfactant adsorption by serum and the mechanisms of reversal by hydrophilic polymers: theory, Biophys J, 89: 1621-1629, 2005.
Zasadzinski, J. et al., Overcoming rapid inactivation of lung surfactant: Analogies between competitive adsorption and colloid stability, Biochimica et Biophysica Acta, 1798, (2010), 801-828.
Amizuka, T. et al., Surfactant therapy in neonates with respiratory failure due to haemorrhagic pulmonary oedema, Eur J Pediatr, 162, (2003), 697-702.

(Continued)

*Primary Examiner* — Jeffrey H Murray
(74) *Attorney, Agent, or Firm* — Greenberg Traurig, LLP

(57) ABSTRACT

Rhodamine dye is delivered to regions of a lung having heterogeneous alveolar flooding by alveolar liquid, thereby lowering the surface tension of the alveolar liquid so as to lessen ventilation injury directly and, by promoting equitable redistribution of the alveolar liquid among the alveoli of the lung, indirectly. The rhodamine dye is delivered with an albumin and/or an exogenous surfactant. Exemplary rhodamine dyes include sulforhodamine B and rhodamine WT.

25 Claims, 22 Drawing Sheets

(56) References Cited

OTHER PUBLICATIONS

Anzueto, A. et al., Aerosolized Surfactant in Adults with Sepsis-Induced Acute Respiratory Distress Syndrome. New Engl J Med 334: 1417-1422, 1996.
Banerjee, R. et al., Ultrastructure of exogenous surfactants using cryogenic scanning electron microscopy, J Biomater Appl, 15, (2001), 230-240.
Batenburg, J. et al., The lipids of pulmonary surfactant: dynamics and interactions with proteins. Prog Lipid Res 37: 235-276, 1998.
Baumgart, F. et al., Palmitoylation of Pulmonary Surfactant Protein SP-C is Critical for Its Functional Cooperation with SP-B to Sustain Compression/Expansion Dynamics in Cholesterol-Containing Surfactant Films, Biophysical Journal, 99, (2010), 3234-3243.
Bernhard, W. et al., Commercial versus Native Surfactants: Surface Activity, Molecular Components, and the Effect of Calcium, Am J Respir Crit Care Med, 162, (2000) 1524-1533.
Berry, D. et al., Respiratory distress and surfactant inhibition following vagotomy in rabbits, J Appl Physiol, 61, (1986), 1741-1748.
Bradbury, J., Could treatment of neonatal RDS improve further?, The Lancet, 360, (2002), p. 394.
Braun, A. et al., A Freeze-Fracture Transmission Electron Microscopy and Small Angle X-Ray Diffraction Study of the Effects of Albumin, Serum and Polymers on Clinical Lung Surfactant Microstructure, Biophysical Journal, 93, (2007)123-139.
Brower, R.G. et al., The Acute Respiratory Distress Syndrome Network. Ventilation with lower tidal volumes as compared with traditional tidal volumes for acute lung injury and the acute respiratory distress syndrome. N Engl J Med 342: 1301-1308, 2000.
Cassidy, K. et al., Liquid Plug Flow in Straight and Bifurcating Tubes, Journal of Biomechanical Engineering, 123, (2001), 580-589.
Clements, J., Lung Surfactant: A Personal Perspective, Annu Rev Physiol, 59, (1997) 1-21.
Curstedt, T. et al., Different Effects of Surfactant Proteins B and C—Implications for Development of Synthetic Surfactants, Neonatology, 97, (2010), 367-372.
De Prost, N. et al., Ventilator-induced lung injury: historical perspectives and clinical implications, Annals of Intensive Care, 1:28, (2011), 1-15.
Dhar, P. et al., Liquid Protein Interactions Alter Line Tensions and Domain Size Distributions in Lung Surfactant Monolayers, Biophysical Journal, 102, (2012), 56-65.
Diemel, R. et al., In vitro and in vivo intrapulmonary distribution of fluorescently labeled surfactant, Crit Care Med, vol. 30, No. 5, (2002), 1083-1090.
Dijk, P. et al., A Comparison of the Hemodynamic and Respiratory Effects of Surfactant Instillation during Interrupted Ventilationversus Noninterrupted Ventilation in Rabbits with Severe Respiratory Failure, Pediatric Research, 45(2), (1999), 235-241.
Ding, J. et al., Effects of Lung Surfactant Proteins, SP-B and SP-C, and Palmitic Acid onMonolayer Stability, Biophysical Journal, 80, (2001), 2262-2272.
Dluhy, R. et al., Deacylated Pulmonary Surfactant Protein SP-C Transforms From a-Helical to Amyloid Fibril Structure via a pH-Dependent Mechanism: An Infrared Structural Investigation, Biophysical Journal, 85, (2003), 2417-2429.
Dreyfuss, D. et al., Ventilator-induced lung injury: lessons from experimental studies. Am J Respir Crit Care Med 157: 294-323, 1998.
Goss, C. et al., Incidence of acute lung injury in the United States, Crit Care Med, vol. 31, No. 6, (2003), 1607-1611.
Greenough, A. Expanded use of surfactant replacement therapy, Eur J Pediatr, 159, (2000), 635-640.
Gregory, T. et al., Surfactant chemical composition and biophysical activity in acute respiratory distress syndrome. J Clin Invest, 88, (1991), 1976-1981.
Gregory, T. et al., Bovine surfactant therapy for patients with acute respiratory distress syndrome, Am J Respir Crit Care Med, 155, (1997), 1309-1315.
Gunther, A. et al., Surfactant alterations in severe pneumonia, acute respiratory distress syndrome, and cardiogenic lung edema. Am J Respir Crit Care Med 153: 176-184,1996.
Gustafsson, M. et al., Amyloid fibril formation by pulmonary surfactant protein C, FEBS Letters, 464, (1999), 138-142.
Gustafsson, M. et al., Palmitoylation of a pulmonary surfactant protein C analogue affects the surface associated lipid reservoir and film stability, Biochimica et Biophysica Acta, 1466 (2000) 169-178.
Gustafsson, M. et al., The Palmitoyl Groups of Lung Surfactant Protein C Reduce Unfolding into a Fibrillogenic Intermediate, J Mol Biol, 310, (2001), 937-950.
Hall, S. et al., Changes in Subphase Aggregates in Rabbits Injured by Free Fatty Acid, Am J Respir Crit Care Med, 149, (1994) 1099-1106.
Halliday, H., Surfactants: past, present and future. J Perinatol 28, Suppl 1: S47-S56, 2008.
Hallman, M. et al., Evidence of lung surfactant abnormality in respiratory failure. Study of bronchoalveolar lavage phospholipids, surface activity, phospholipase activity, and plasma myoinositol, J Clin Invest, 70: 673-683, 1982.
Heldt, G. et al., Distribution of Surfactant, Lung Compliance, and Aeration of Preterm Rabbit Lungs after Surfactant Therapy and Conventional and High-Frequency Oscillatory Ventilation, Pediatric Research, vol. 31, No. 3, (1992), 270-275.
Henry, M. et al., Ultrasonic Nebulized in Comparison with Instilled Surfactant Treatment of Preterm Lambs, Am J Respir Crit Care Med, 154, (1996), 366-375.
Holm, B. et al., Content of Dipalmitoyl Phosphatidylcholine in Lung Surfactant: Ramifications for Surface Activity, Pediatric Research, 39(5), (1996), 805-811.
Holm, B. et al., A biophysical mechanism by which plasma proteins inhibit lung surfactant activity, Chem Phys Lipids, 49, (1988) 49-55.
Ikegami, M. et al., A Protein That Inhibits Surfactant in Respiratory Distress Syndrome, Biol Neonate, 50, (1986), 121-129.
Jobe, A. et al., Lung protein leaks in ventilated lambs: effects of gestational age, Journal of Applied Physiology, vol. 58, No. 4, (1985), 1246-1251.
Jobe, A. et al., Permeability of premature lamb lungs to protein and the effect of surfactant on that permeability, Journal of Applied Physiology, vol. 55, No. 1, (1983), 169-176.
Johansson, J. et al., Molecular structures and interactions of pulmonary surfactant components, Eur J Biochem 244: 675-693,1997.
Jordanova, A. et al., Influence of surfactant protein C on the interfacial behavior of phosphatidylethanolamine monolayers, Eur Biophys J, 38, (2009), 369-379.
Kesecioglu, J. et al., Exogenous natural surfactant for treatment of acute lung injury and the acute respiratory listress syndrome, Am J Respir Crit Care Med, 180: 989-994, 2009.
Kharge, A. et al., Sulforhodamine B interacts with albumin to lower surface tension and protect against ventilation injury of flooded alveoli. J Appl Physiol, 118, (2015), 355-364.
Kharge, A. et al., Surface tension in situ in flooded alveolus unaltered by albumin, J Appl Physiol, 117: 440-451, 2014.
Kitamura, M. et al., Binding of sulforhodamine B to human serum albumin: a spectroscopic study, Dyes Pigments, 99: 588-593, 2013.
Kovacs, H. et al., The Effect of Environment on the Stability of an Integral Membrane Helix: Molecular Dynamics Simulations of Surfactant Protein C in Chloroform, Methanol and Water, J Mol Biol, 247, (1995), 808-822.
Krause, M. et al., Alveolar Recruitment Promotes Homogeneous Surfactant Distribution in a Piglet Model of Lung Injury, Pediatric Research, vol. 50, No. 1, (2001), 34-43.
Landmann, E. et al., Protein content and biophysical properties of tracheal aspirates form nennates with respiratory failure, Klin Padiatr, 214, (2002), 1-7.
Lewis, J. et al., Altered Alveolar Surfactant Is an Early Marker of Acute Lung Injury in Septic Adult Sheep, American Journal of Respiratory and Critical Care Medicine, vol. 150, No. 1, (1994), 123-130.
Lewis, J. et al., Lung function and surfactant distribution in saline-lavaged sheep given instilled vs. nebulized surfactant, Journal of Applied Physiology, vol. 74, No. 3, (1993), 1256-1264.

(56) References Cited

OTHER PUBLICATIONS

Li, J. et al., The N-terminal Propeptide of Lung Surfactant Protein C is Necessary for Biosynthesis and Prevents Unfolding of a Metastable a-Helix, J Mol Biol, 338, (2004), 857-862.

Liau, D. et al., Functional Abnormalities of Lung Surfactant in Experimental Acute Alveolar Injury in the Dog, Am Rev Respir Dis, 136, (1987), 395-401.

Lukovic, D. et al., Production and characterisation of recombinant forms of human pulmonary surfactant protrain C (SP-C): Structure and surface activity, Biochimica et Biophysica Acta, 1758, (2006), 509-518.

Mazela, J. et al,. Comparison of poractant alfa and lyophilized lucinactant in a preterm lamb model of acute respiratory distress, Pediatric Research, vol. 72, No. 1, (2012), 32-37.

Moison, R. et al., Plasma Proteins in Acute and Chronic Lung Disease of the Newborn, Free Radical Biology & Medicine, vol. 25, No. 3, (1998), 321-328.

Morley, C., Systematic review of prophylactic vs rescue surfactant, Archives of Disease in Childhood, 77, (1997), F70-F74.

Nakamura, H. et al., Monomolecular surface film and tubular myelin figures of the pulmonary surfactant in hamster lung, Cell Tissue Res, 241, (1985), 523-528.

Nicholas, T. Pulmonary Surfactant: No mere paint on the alveolar wall, Respirology, 1, (1996), 247-257.

Niemarkt, H. et al., Effects of less-invasive surfactant administration on oxygenation, pulmonary surfactant distribution, and lung compliance in spontaneously breathing preterm lamb, Pediatric Research, 76, (2014), 166-170.

Notter, R. et al., Biophysical Activity of Synthetic Phospholipids Combined with Purified Lung Surfactant 6000 Dalton Apoprotein, Chemistry and Physics of Lipids, 44, (1987) 1-17.

Otsubo, E. et al., Characterization of the Surface Activity of a Synthetic Surfactant with Albumin, Biol Pharm Bull, 25 (12), (2002), 1519-1523.

Petty, T. et al., Abnormalities in Lung Elastic Properties and Surfactant Function in Adult Respiratory-Distress Syndrome. Chest 75: 571-574, 1979.

Petty, T. et al., Characteristics of Pulmonary Surfactant in Adult Respiratory Distress Syndrome Associated with Trauma and Shock, American Review of Respiratory Disease, 115, (1977), 531-536.

Phua, J. et al., Has mortality from acute respiratory distress syndrome decreased over time?: A systematic review, Am J Respir Crit Care Med, 179: 220-227, 2009.

Pison, U. et al., Surfactant Abnormalities in Patients with Respiratory Failure after Multiple Trauma, Am Rev Respir Dis, 140: 1033-1039, 1989.

Plasencia, I. et al., The N-terminal segment of pulmonary surfactant lipopeptide SP-C hasintrinsic propensity to interact with and perturb phospholipid bilayers, Biochem J, 377, (2004), 183-193.

Polat, B. et al., An experimental and molecular dynamics investigation into the amphiphilic nature of sulforhodamine B, J Phys Chem B, 115: 1394-1402, 2011.

Product Monograph, Curosurf, Chiesi Farmaceutici, Parma, Italy, Sep. 2009.

Robertson, B. et al., Principles of surfactant replacement, Biochimica et Biophysica Acta, 1408, (1998) 346-361.

Rooney, S., Lung Surfactant, Environmental Health Perspectives, 55, (1984), 205-226.

Rubenfeld, G. et al., Incidence and outcomes of acute lung injury, N Engl J Med, 353: 1685-1693, 2005.

Sarin, V. et al., Biophysical and biological activity of a synthetic 8.7-kDa hydrophobic pulmonary surfactant protein SP-B, Proc Natl Acad Sci USA, 87, (1990), 2633-2637.

Schmidt, R. et al., Alteration of fatty acid profiles in different pulmonary surfactant phospholipids in acute respiratory distress syndrome and severe pneumonia, Am J Respir Crit Care Med, 163: 95-100, 2001.

Scientific Committee on Consumer Products (SCCP), Health and Consumer Protection Directorate-General, European Commission. Opinion on Acid Red 52 (Online). http://ec.europa.eu/health/ph_risk/committees/04_sccp/docs/sccp_o_137.pdf [Jun. 24, 2008].

Seeger, W. et al., Alveolar surfactant and adult respiratory distress syndrome, Clin Investig, 71, (1993), 177-190.

Seeger, W. et al., Surfactant inhibition by plasma proteins: differential sensitivity of various surfactant preparations, Eur Respir J, 6, (1993), 971-977.

Seeger, W. et al., Differential sensitivity to fibrinogen inhibition of SP-C- vs. SP-B-based surfactants, Am J Physiol Lung Cell Mol Physiol, 262: L286-L291, 1992.

Seeger, W. et al., Alteration of surfactant function due to protein leakage: special interaction with fibrin monomer, J Appl Physiol, 58: 326-338, 1985.

Seehase, M. et al, New Surfactant with SP-B and C Analogs Gives Survival Benefit after Inactivation in Preterm Lambs, PLoS ONE, 7(10), (2012), e47631.

Segerer, H. et al., Rapid Tracheal Infusion of Surfactant versus Bolus Instillation in Rabbits: Effects on Oxygenation, Blood Pressure and Surfactant Distribution, Biol Neonate, 69, (1996), 119-127.

Smart, P. et al., An Evaluation of Some Fluorescent Dyes for Water Tracing, Water Resources Research, vol. 13, No. 1, (1977), 15-33.

Smart, P., A review of the toxicity of twelve fluorescent dyes used for water tracing, NSS Bulletin, 46: 21-33, 1984.

Speer, C. et al., Early versus late surfactant therapy in severe respiratory distress syndrome, Lung, Suppl, (1990), 870-876.

Spragg, R. et al., Effect of recombinant surfactant protein C-based surfactant on the acute respiratory distress syndrome, N Engl J Med, 351: 884-892, 2004.

Spragg, R. et al., Surfactant Replacement Therapy, Clinics in Chest Medicine, vol. 21, No. 3, (2000), 531-541.

Spragg, R. et al., Recombinant surfactant protein C-based surfactant for patients with severe direct lung injury, Am J Respir Crit Care Med, 183: 1055-1061, 2011.

St. Clair, C. et al., The Probability of Neonatal Respiratory Distress Syndrome as a Function ofGestational Age and Lecithin/Sphingomyelin Ratio, American Journal of Perinatology, vol. 25, No. 8, (2008), 473-480.

Szyperski, T. et al., Pulmonary surfactant-associated polypeptide C in a mixed organic solvent transforms from a monomeric a-helical state into insoluble P-sheet aggregates, Protein Science, 7, (1998), 2533-2540.

Taeusch, H. et al., Inactivation of pulmonary surfactant due to serum-inhibited adsorption and reversal by hydrophilic polymers: Experimental, Biophys J, 89: 1769-1779, 2005.

Takahashi, A. et al Structure-function relationships of bovine pulmonary surfactant proteins: SP-B and SP-C, Biochim Biophys Acta, 1044: 43-49, 1990.

Tanaka, Y. et al., Lung Surfactants. II. Effects of fatty acids, triacylglycerols and protein on the activity of lung surfactant, Chemical and Pharmaceutical Bulletin, vol. 31, No. 11, (1983), 4100-4109.

Terry, M. et al., Pulmonary Distribution of Lucinactant and Poractant Alfa and Their Peridosing Hemodynamic Effects in a Preterm Lamb Model of Respiratory Distress Syndrome, Pediatric Research, vol. 68, No. 3, (2010), 193-198.

Tierney, D. et al., Altered surface tension of lung extracts and lung mechanics, J Appl Physiol, 20: 1253-1260, 1965.

Tsuda, S. et al., DNA damage induced by red food dyes orally administered to pregnant and male mice, Toxicol Sci, 61: 92-99, 2001.

Ueda, T. et al., Distribution of surfactant and ventilation in surfactant-treated preterm lambs, Journal of Applied Physiology, vol. 76, No. 1, (1994), 45-55.

Veldhuizen, R. et al., Pulmonary surfactant subfractions in patients with the acute respiratory distress syndrome, Am J Respir Crit Care Med, 152: 1867-1871, 1995.

Von Nahmen, A. et al., The phase behavior of lipid monolayers containing pulmonary surfactant protein C studied by fluorescence light microscopy, Eur Biophys, J, 26, (1997), 359-369.

Voss, T. et al., Primary structure differences of human and surfactant-associated proteins isolated from normal and proteinosis lung, Biochimica et Biophysica Acts, 1138, (1992), 261-267.

(56) References Cited

OTHER PUBLICATIONS

Walther, F. et al., Hydrophobic Surfactant Proteins and Their Analogues, Neonatology, 91, (2007), 303-310.

Walther, F. et al., (2014), Surfactant protein C peptides with salt-bridges ("ion-locks") promote high surfactant activities by mimicking the α-helix and membrane topography of the native protein, PeerJ 2:e485; DOI 10.7717/peerj.485, published Jul. 15, 2014.

Walther, F. et al., A Synthetic Segment of Surfactant Protein A: Structure, in Vitro Surface Activity, and in Vivo Efficacy, Pediatric Research, 39(6), (1996), 938-946.

Non-Final Office Action issued Dec. 11, 2015 in U.S. Appl. No. 13/650,759.

Bachofen et al., "Experimental Hydrostatic Pulmonary Edema in Rabbit Lungs", The American Review of Respiratory Disease, vol. 147, (1993), pp. 989-996.

Brower et al., "Another "Negative" Trial of Surfactant, Time to Bury this Idea?", American Journal of Respiratory and Critical Care Medicine, vol. 183, (2011), pp. 966-968.

Cairo et al., "Mosby's Respiratory Care Equipment (Eighth Edition)", 2011, pp. 217-228; 223-238; 377; 398-403 and D 685.

Diemel, R. et al., In vitro and in vivo intrapulmonary distribution of fluorescently labeled surfactant, Grit Care Med, vol. 30, No. 5, (2002), 1083-1090.

Gu, J. et al., (2007). Pathology and pathogenesis of severe acute respiratory syndrome. The American journal of pathology, 170(4), 1136-1147.

Krishnan et al., "High-Frequency Ventilation for Acute Lung Injury and ARDS", Chest, vol. 118, No. 3, Sep. 2000, pp. 795-807.

National Center for Biotechnology Information. PubChem Compound Database; CID=65191, https://pubchem.ncbi.nlm.nik.gov/compound/65191 (accessed May 6, 2016.

Perlman et al., "Micromechanics of Alveolar Edema", American Journal of Respiratory Cell Molecular Biology, vol. 44, (2011) pp. 34-39.

Scientific Committee of Consumer Products (SCCP), Health and Consumer Protection Directorate-General, European Commission. Opinion on Acid Red 52 (Online). http://ec.europe.eu/health/ph_risk/committees/04_sccp/docs/sccp_o_137.pdf [pdf Jun. 24, 2008].

Staub et al., "Pulmonary edema in dogs, especially the sequence of fluid accumulation in lungs", Journal of Applied Physiology, vol. 22, No. 2, (1967), pp. 227-240.

Stawicki et al., "High-Frequency Oscillatory Ventilation (HFOV) and Airway Pressure Release Ventillation (APRV): A Practical Guide", Journal of Intensive Care Medicine, vol. 24, No. 4, Jul./Aug. 2009, pp. 215-229.

Tsuchida et al., "Atelectasis Causes Alveolar Injury in Nonatelectatic Lung Regions", American Journal of Respiratory Critical Care Medicine, vol. 174, (2006), pp. 279-289.

Varisco, B. M. (2011), The pharmacology of acute lung injury in sepsis. Advances in pharmacological sciences, 2011.

Wilkins et al., "Egan's Fundamentals of Respiratory Care", Mosby, Inc. (2009), pp. 939-941.

$$P_{LIQ-EDEM} = P_{ALV} - 2T/R_{MENISC}$$
$$\Delta P_{BARRIER} = P_{LIQ-BORD} - P_{LIQ-EDEM} = 2T(1/R_{MENISC} - 1/R_{BORD}) > 0$$

Baseline | 0 min | 5 min | 10 min
Five Ventilation Cycles | Time Post Ventilation
(Constant 5 cmH$_2$O Inflation Pressure)

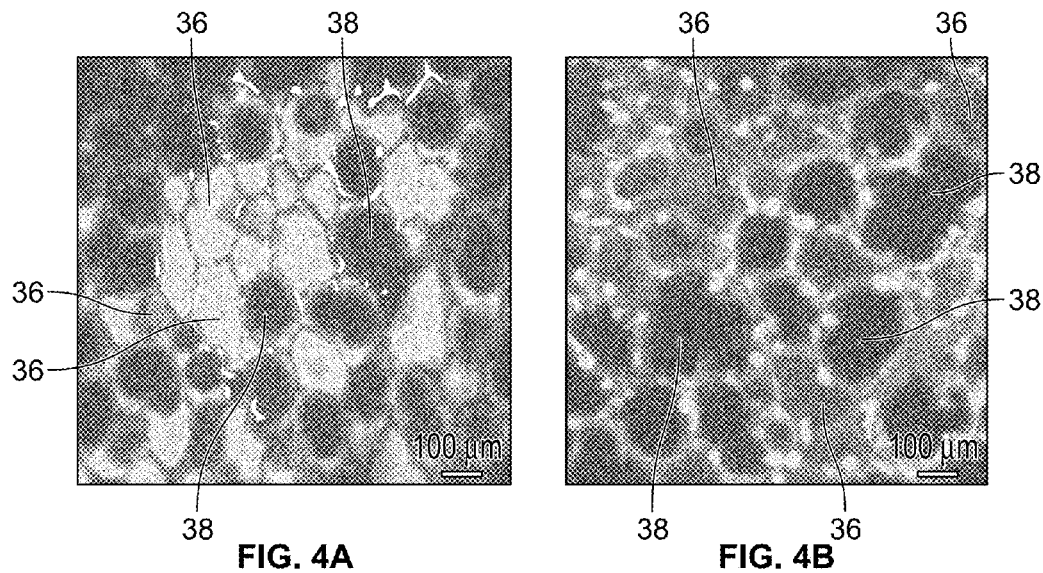
FIG. 4A  FIG. 4B
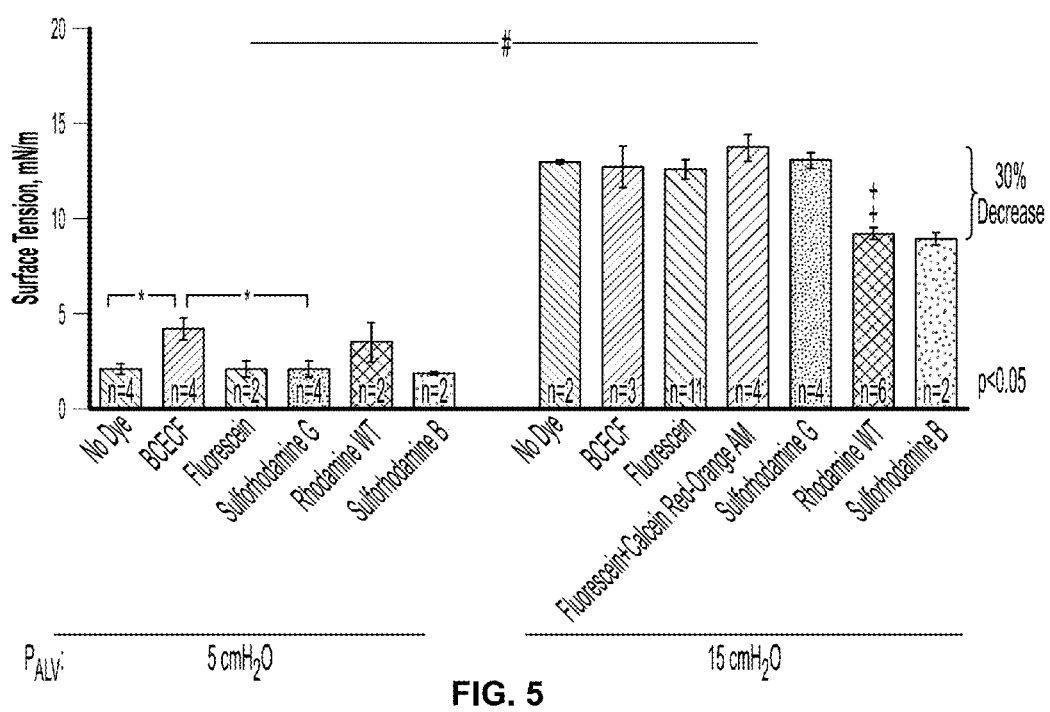
FIG. 5

Lung Tissue
Liquid
* Liquid-filled Airway
**Open Airway

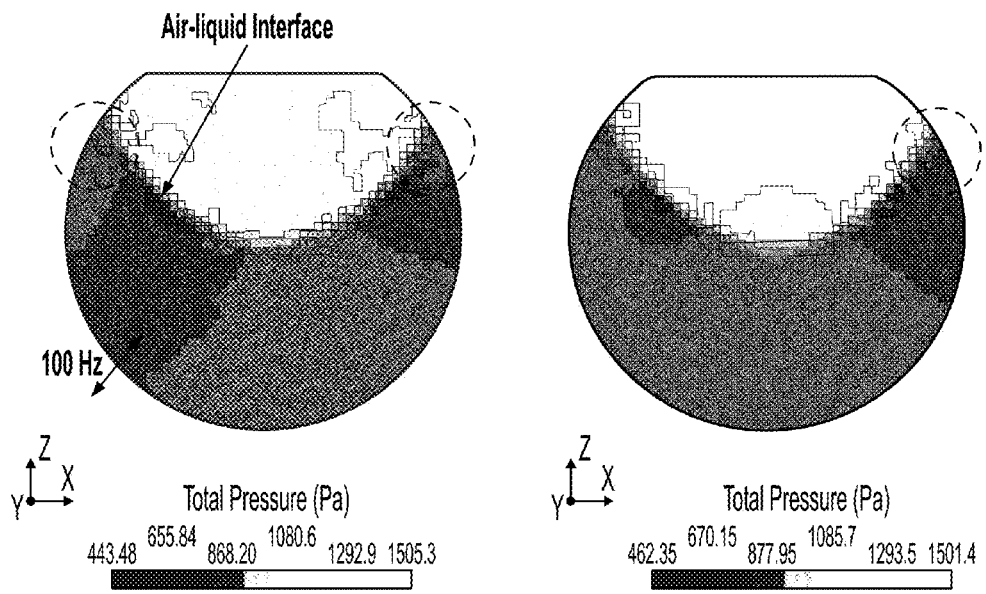
FIG. 19A  FIG. 19B
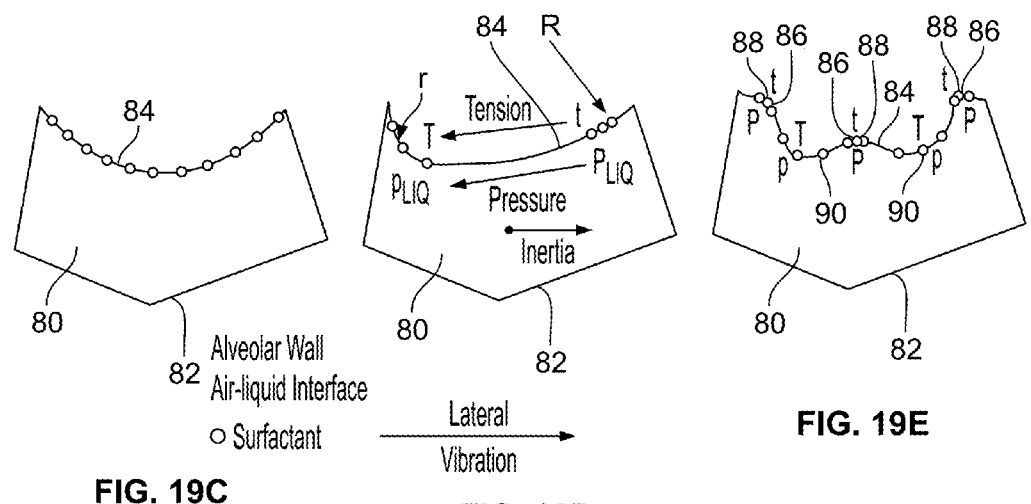
FIG. 19C  FIG. 19D  FIG. 19E

USE OF RHODAMINE DYES TO REDUCE ALVEOLAR SURFACE TENSION

CROSS-REFERENCE TO RELATED APPLICATIONS

The present application claims the benefit of U.S. Provisional Patent Application No. 62/079,004, filed on Nov. 13, 2014, and is a continuation-in-part of U.S. patent application Ser. No. 13/650,759, filed on Oct. 12, 2012, which claims the benefit of U.S. Provisional Patent Application No. 61/547,133, filed on Oct. 14, 2011, all of which are incorporated by reference herein in their entireties.

FIELD OF THE INVENTION

The present invention relates to a means of reducing alveolar surface tension and methods for promoting equitable liquid distribution amongst pulmonary alveoli in the presence of alveolar edema, all of which contribute to reducing ventilator-induced lung injury.

BACKGROUND OF THE INVENTION

Physiology and Pathophysiology

Lung Physiology.

The terminal airspaces of the lungs, the alveoli, are lined with a thin liquid lining layer. Thus there is an air-liquid interface in the lungs that has an associated surface tension. Alveolar type II epithelial cells release lung surfactant—an aggregate of phospholipids and proteins—into the liquid lining layer. The surfactant adsorbs to and reduces surface tension at the air-liquid interface. By lowering surface tension, surfactant reduces the pressure required to keep the lungs inflated and reduces the work of breathing.

ARDS.

The acute respiratory distress syndrome (ARDS), can result from a variety of initial insults. ARDS has an incidence of about 200,000 cases per year in the United States, with a mortality rate exceeding 35%. For the purpose of the present disclosure, ARDS includes acute lung injury (ALI), which has been reclassified as mild ARDS.

In ARDS, inflammation is present in the lungs. With inflammation, pulmonary vascular permeability increases and liquid leaks out of the blood vessels into the surrounding interstitial tissue. The liquid carries plasma proteins with it. When enough liquid escapes from the vessels, liquid begins to enter the alveoli, a condition known as alveolar edema. Initially, discrete alveoli in the dependent (bottom portion of the) lung become flooded and are interspersed with alveoli that remain aerated. With disease progression, most alveoli in the dependent lung become flooded; in the nondependent lung, some alveoli become flooded and are interspersed with other alveoli that remain aerated. From the onset of edema, the additional liquid in the interstitium and airspace effectively thickens the alveolar-capillary membrane across which oxygen and carbon dioxide must pass, making gas exchange difficult. Further, in ARDS, lung compliance is reduced, which makes breathing difficult.

ARDS patients are treated by mechanical ventilation, which assists gas exchange and keeps patients alive but often causes an over-distension injury (ventilator-induced lung injury, VILI) that exacerbates the underlying lung disease and prevents patient recovery. It is now standard protocol to ventilate with a low tidal (breath) volume that has been shown to decrease mortality. However, mortality still exceeds 35%.

It has been hoped that administration of exogenous surfactant would reduce surface tension, increase lung compliance and protect against VILI. Thus, multiple randomized clinical trials have tested tracheal administration of exogenous surfactant in ARDS patients. However, exogenous surfactant administration has not reduced mortality, excepting in one pediatric study.

In VILI, the site of over-distension injury is likely in aerated alveoli adjacent to flooded alveoli. In flooded alveoli, the air-liquid interface forms a concave meniscus. Due to surface tension at the meniscus and pressure drop across the meniscus, flooded alveoli are shrunken and adjacent aerated alveoli are, due to interdependence, expanded. Mechanical ventilation significantly exacerbates the over-expansion of aerated alveoli located adjacent to flooded alveoli.

Neonatal Respiratory Distress Syndrome (RDS).

Surfactant production increases markedly during the third trimester of gestation. Premature babies born prior to or early in the third trimester used not to survive. Since the 1980's, tracheal instillation of exogenous surfactant has enabled such premature babies to live. However, there remains room for improvement in the clinical treatment of neonatal RDS.

High Frequency Modes of Lung Treatment.

For various objectives such as loosening/clearance of airway mucus and improved mechanical ventilation, the lung has sometimes been subjected to percussion or to high frequency ventilation. Devices designed to implement such treatments, and the frequencies at which they operate, include: pneumatically and electrically powered percussors; intrapulmonary percussive ventilation (1.7-5 Hz); flutter valve therapy; high-frequency chest wall oscillation (5-25 Hz); high frequency positive-pressure ventilation (1-1.8 Hz); high-frequency jet ventilation (up to 10 Hz); high-frequency oscillatory ventilation (1-50 Hz); high-frequency flow interruption (up to 15 Hz, where the flow interruption occurs during inspiration, not expiration); and high-frequency percussive ventilation (up to 2 Hz). None of these 'high-frequency' treatments operate at a frequency greater than 50 Hz.

Active Deflation.

Certain existing modes of mechanical ventilation have incorporated active deflation. Although now out of use, ventilation with negative end-expiratory pressure (NEEP)—available on Puritan Bennett AP series and Bird Mark 7 and 8 ventilators—can use a Venturi tube to actively draw air out of the airways and lower the minimal tracheal entrance pressure at end-expiration below atmospheric pressure. In a Venturi tube, a high pressure gas jet is forced through a small orifice at the tube end while a different gas enters through a second port at lower velocity. The jet accelerates the lower velocity gas by entrainment.

High-frequency oscillatory ventilation uses an oscillator to move a diaphragm at one end of a chamber that is incorporated into the mechanical ventilation circuit proximal to the endotracheal tube. On its forward stroke the oscillator compresses air within the chamber; on its backward stroke it expands air within the chamber. During the backward stroke, tracheal pressure may become negative. HFOV is most frequently used in neonatal ventilation, although it is used in adults as well.

SUMMARY OF THE INVENTION

In one aspect of the present invention, a surface tension-lowering agent is added to alveolar edema liquid to (i)

directly lessen ventilation-induced over-distension injury of aerated alveoli located adjacent to flooded alveoli and (ii) promote equitable edema liquid redistribution among alveoli. Such surface tension lowering agents may include certain rhodamine dyes.

In another aspect of the present invention, an active, accelerated deflation method is applied during mechanical ventilation of the edematous lungs to promote equitable edema liquid redistribution between alveoli. An embodiment of the present invention includes an apparatus for generating such pressure waveforms.

In yet another aspect of the present invention, high frequency vibration of, or step or impulse force application to, the edematous lungs promotes equitable edema liquid redistribution among alveoli. Such vibrations, or step or impulse forces, may be applied by various means.

BRIEF DESCRIPTION OF THE DRAWINGS

For a more complete understanding of the present invention, reference is made to the following detailed description of exemplary embodiments considered in conjunction with the accompanying drawings, in which:

FIGS. 4A and 4B are a pair of enhanced micrographs showing a local alveolar edema model and a global permeability edema model in experiments performed to demonstrate an embodiment of the present invention;

FIG. 5 is a bar chart comparing the effect of dye inclusion on surface tension in alveoli flooded with albumin solution at two transpulmonary pressures in experiments performed to demonstrate an embodiment of the present invention;

FIGS. 19A and 19B are a pair of schematic images generated by a computational fluid dynamics model, representing the effect of vibrating a flooded alveolus according to an embodiment of the present invention;

FIGS. 19C, 19D, and 19E are a group of schematic drawings illustrating a conceptual model of the effect of vibration on edematous alveolar surface tension, performed according to an embodiment of the present invention, on edematous alveolar surface tension;

DETAILED DESCRIPTION OF THE INVENTION

Figure 1:
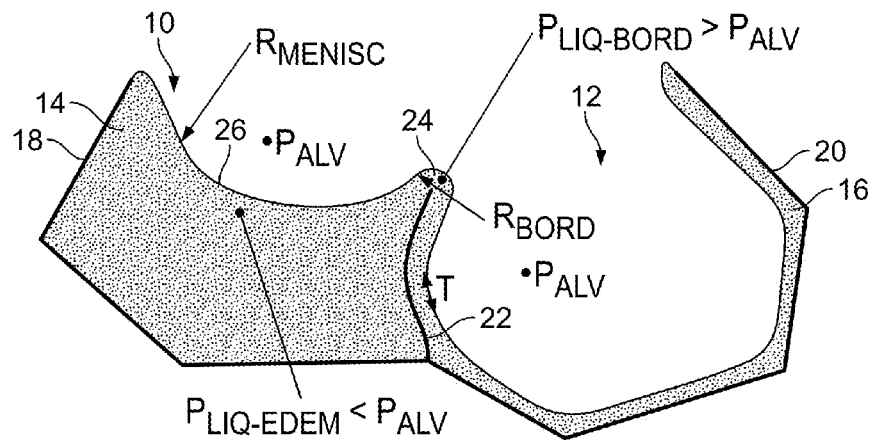
FIG. 1 is a schematic illustration of a novel analysis of regional liquid phase pressures in an edematous alveolus adjacent to an aerated alveolus, made according to an embodiment of the present invention.

FIG. 1 is a schematic drawing of regional liquid-phase pressures in an edematous (i.e., flooded) alveolus 10 adjacent to an aerated alveolus 12, according to a novel analysis of the mechanics of alveolar edema by the inventor of the present invention. The shaded areas 14, 16 represent liquid. The dark lines represent alveolar wall 18, 20, 22, where alveolar wall 22 is also a septum 22 between the edematous alveolus 10 and the aerated alveolus 12. As the liquid lining layer is continuous between alveoli, such as alveoli 10, 12, the edema liquid 14 of the edematous alveolus 10 is continuous with the liquid lining layer 16 of the aerated alveolus 12. By the Laplace relation, $P_{ALV} > P_{LIQ\text{-}EDEM}$, where $P_{ALV}$ is alveolar air pressure and $P_{LIQ\text{-}EDEM}$ is liquid pressure in the edematous alveolus, and the difference between the two pressures is proportional to surface tension T. Thus, pressure is greater in the aerated alveolus 12, where air pressure is the same $P_{ALV}$ as in the edematous alveolus 10, than in the edematous alveolus 10. Due to pressure imbalance, the septum 22 between the two alveoli 10, 12 bows into the edematous alveolus 10 causing that alveolus 10 to shrink and the aerated alveolus 12 to be expanded. Further, the free end of the septum 22 between the two alveoli 10, 12, has a saddle shaped geometry that should cause the air-liquid interface at the border 24 between the alveoli to have a small, convex radius of curvature $R_{BORD}$ in the plane of FIG. 1 and a larger concave radius of curvature (not shown) in a plane perpendicular to that of FIG. 1. Due to this geometry, $P_{LIQ\text{-}BORD} > P_{ALV}$, where $P_{LIQ\text{-}BORD}$ is liquid pressure at the border 24 between the edematous and aerated alveoli 10, 12. Thus $P_{LIQ\text{-}BORD} > P_{LIQ\text{-}EDEM}$, forming a pressure barrier to liquid flow out of the edematous alveolus 10. The magnitude of the pressure barrier, $\Delta P_{BARRIER} = P_{LIQ\text{-}BORD} - P_{LIQ\text{-}EDEM}$, is determined by the Laplace relation and is proportional to the interfacial surface tension, T.

Figure 2A:
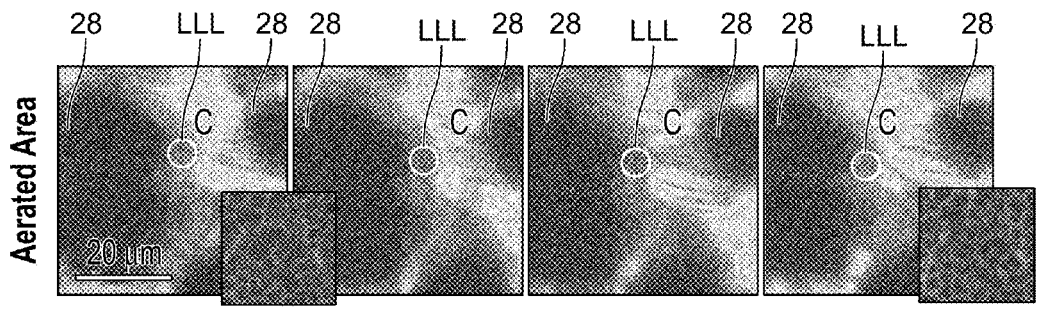
FIG. 2A is series of microphotographs showing an aerated control area of a lung where a liquid has been microinjected periodically into a group of surface alveoli to avoid persistence of alveolar flooding in an experiment performed to demonstrate an embodiment of the present invention.
Figure 2B:
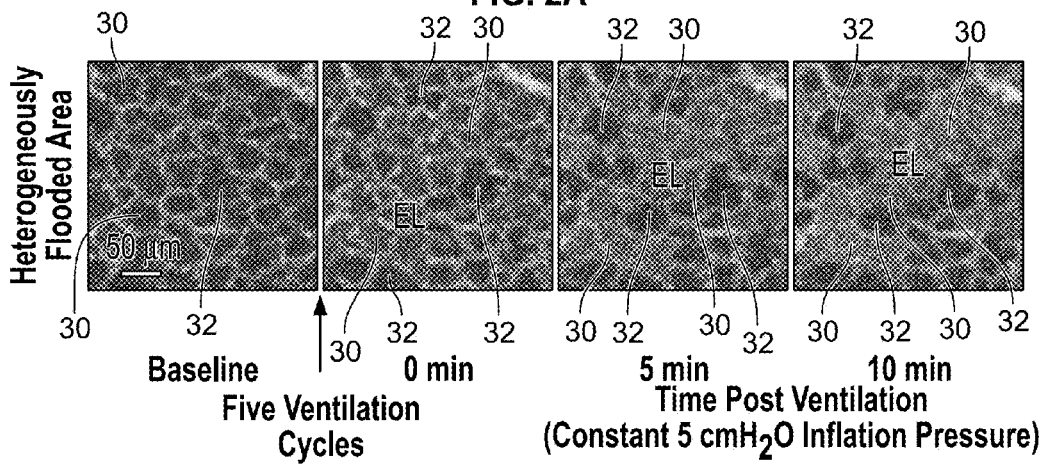
FIG. 2B is a series of microphotographs showing a heterogeneously flooded experimental area of a lung where a liquid has been continuously delivered into a group of surface alveoli to generate a local model of alveolar edema in an experiment performed to demonstrate an embodiment of the present invention.
Figure 2C:
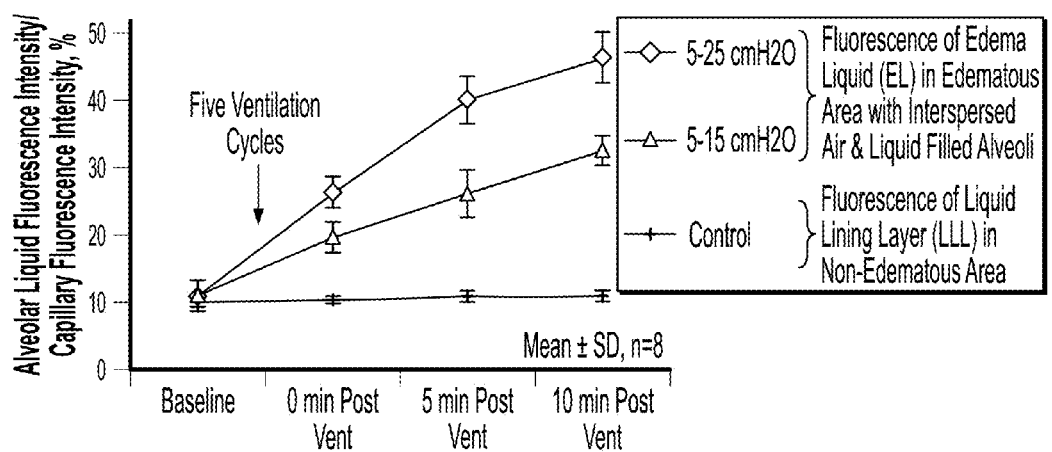
FIG. 2C is a graph showing grouped fluorescence-intensity data indicative of ventilation-induced injury to control aerated and heterogeneously flooded experimental lung areas, for two different sets of ventilation pressure limits in an experiment performed to demonstrate an embodiment of the present invention.

Further, the degree of over-expansion of the aerated alveolus is injurious. FIGS. 2A-2C demonstrate that in the presence of heterogeneous alveolar flooding ventilation causes sustained injury (i.e., VILI) to the alveolar-capillary barrier.

Referring to FIGS. 2A and 2B, the isolated, perfused rat lung model was prepared, with fluorescein (31 μM) included in the perfusate to label the capillaries (C). A glass micropipette was filled with non-fluorescent normal saline with 5% fatty acid-bound bovine serum albumin (BSA). The tip of the micropipette was inserted into a surface alveolus and the solution was microinjected into a group of surface alveoli either periodically, such that the fluid cleared from all alveoli to leave a control micropunctured-but-aerated area, or continuously, such that the fluid cleared from some but not all alveoli to leave an experimental heterogeneously flooded area. The area was imaged by confocal microscopy at $P_{ALV}$ of 5 cmH$_2$O. The lungs were ventilated five times between $P_{ALV}$ of 5 and 25 cmH$_2$O and then returned to a constant $P_{ALV}$ of 5 cmH$_2$O for 10 min of additional imaging. The five ventilation breaths generated an over-distension injury in areas of heterogeneous alveolar flooding, as evidenced by movement of fluorescein from the vasculature into the alveolar liquid that continued even after the lungs were returned to a constant, low volume.

The micrographs of FIG. 2A show a control aerated area of a rat lung. White circles label an area of the alveolar liquid lining layer (LLL) and insets show a lower magnification of the alveolar field. The micrographs of FIG. 2B show an experimental area with heterogeneous flooding (flooded alveoli are not visible at baseline, as flooding solution was not fluorescent). Post ventilation, LLL fluorescence remained unchanged in the aerated area but alveolar liquid fluorescence increased in the heterogeneously flooded area. Once flooded alveoli become evident following ventilation, aerated alveoli in the heterogeneously flooded region also become evident. Exemplary aerated alveoli are shown as dark areas 32. Further, over the 10 min of imaging post ventilation with the lungs held at constant, low inflation volume, alveolar liquid fluorescence continued to increase, indicating the injury was not transient, but sustained.

FIG. 2C is a graph, showing grouped data for the tests described with relation to FIGS. 2A and 2B for two different sets of ventilation pressure limits and in which alveolar liquid fluorescence intensity is normalized by capillary fluorescence intensity. Error bars indicate standard deviation. These data demonstrate that the means of detecting VILI discussed above is sensitive to the severity of the mechanical ventilation applied to the lungs.

As discussed with respect to FIG. 2 above, lung ventilation injures areas with heterogeneous alveolar flooding. The theory of FIG. 1 suggests that aerated alveoli in heterogeneously flooded areas are over-distended to a degree that is proportional to surface tension, thus that ventilation injury is proportional to surface tension. As surface tension increases with lung inflation, the data of FIG. 2B showing that ventilation to a higher peak lung inflation pressure is more injurious support the theory of FIG. 1 that the injury is proportional to surface tension. Therefore, lessening surface tension should directly lessen ventilation injury of the lungs.

Figure 3:
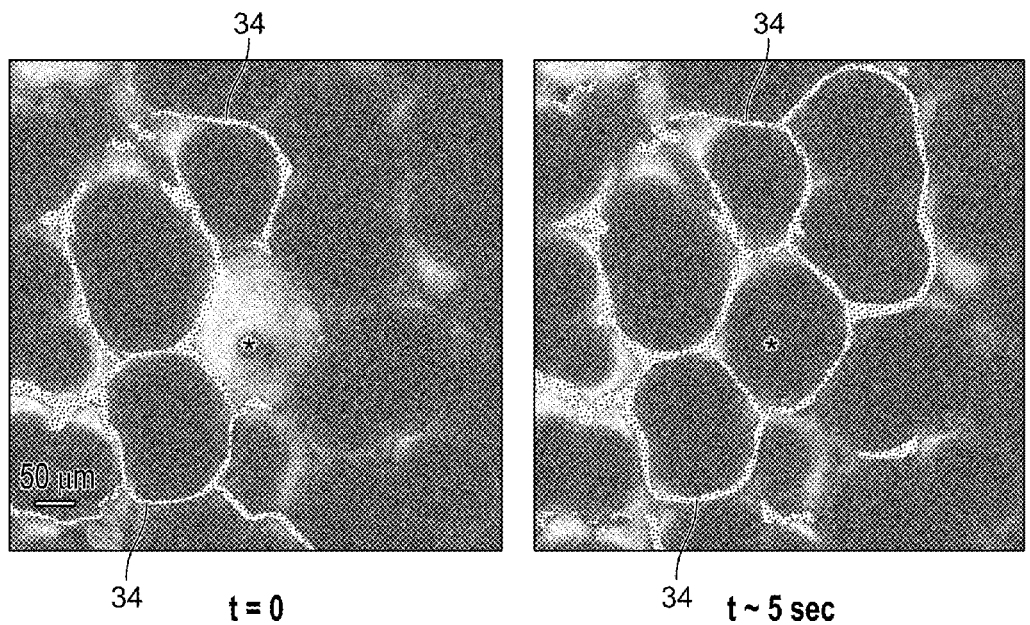
FIG. 3 is a pair of micrographs depicting a flooded alveolus that has spontaneously cleared.

The theory of FIG. 1 and data of FIG. 2 also suggest that if areas with heterogeneous alveolar flooding are the site of ventilation injury then redistributing edema liquid more equitably among alveoli would, by equalizing forces across more septa between alveoli, indirectly protect against ventilation injury. Flooded alveoli, which are shrunken, are generally stable but occasionally spontaneously clear. When flooded alveoli clear they instantaneously "pop" open as liquid disperses to nearby alveoli. That is, the liquid from alveoli that "clear" is equitably redistributed amongst surrounding alveoli. Referring to FIG. 3, a pair of micrographs depicts the spontaneous clearing of a flooded alveolus, indicated by an asterisk (*). The micrographs are sequential optical sections from a z-stack of images, with a time of about 5 sec between images. In between imaging the two sections, the liquid cleared from the (*) alveolus, leaving it aerated. In FIG. 3, the lightly-stippled areas 34 represent liquid in or adjacent to alveolar walls.

That flooded alveoli occasionally spontaneously clear suggests that the flooded state is a local, but not global, equilibrium. Thus it may be possible to overcome the pressure barrier $\Delta P_{BARRIER}$—equal to $P_{LIQ\text{-}BORD}$ at the border between two alveoli minus $P_{LIQ\text{-}EDEM}$ within the edematous alveolus and discussed above with respect to FIG. 1—that opposes the escape of liquid from discretely flooded alveoli. Means of overcome $\Delta P_{BARRIER}$ should promote liquid escape from flooded alveoli, thus promote more equitable edema liquid distribution between alveoli and, indirectly, protect against ventilation injury. As the magnitude of $\Delta P_{BARRIER}$ is proportional to the interfacial surface tension, lowering surface tension should be one means of overcoming $\Delta P_{BARRIER}$.

To protect against ventilator-induced lung injury, the various aspects of the present invention provide approaches to reduce alveolar over-distension both directly, by lowering surface tension, and indirectly, by overcoming $\Delta P_{BARRIER}$ to promote equal liquid distribution among alveoli. Such approaches include, but are not necessarily limited to:

1. Surface tension reduction, which includes administering an additive alone or with instilled exogenous surfactant and/or facilitating agent (e.g. supplemental albumin) to reduce surface tension, thus directly reducing ventilation injury and also lowering the pressure barrier to promote equitable edema liquid distribution among alveoli;
2. Active deflation during mechanical ventilation, which includes the use of active, accelerated deflation in combination with maintenance of a positive end-expiratory pressure (PEEP) to transiently increase $P_{LIQ\text{-}EDEM}$ and reduce the pressure barrier; and
3. Vibration or step or impulse force application to the lungs, which includes vibrating the lungs or applying a step or impulse force to the lungs to impose spatial variation in surface tension and/or to perturb the normal pressure gradient in the alveolar edema liquid, and, in a random fashion, increase the likelihood of overcoming the pressure barrier to cause edematous alveolar clearance.

1. Surface Tension Reduction

Additives to alveolar flooding liquid were tested in the isolated rat lung model for their ability to reduce surface tension. FIGS. 4A and 4B are a pair of micrographs showing two alveolar edema models. The model of FIG. 4A is a local edema model that can be generated in the perfused (perfusate comprises 10 ml of autologous blood plus 18 ml of 5% fatty acid-bound BSA in normal saline) or unperfused lung by alveolar microinjection of a flooding solution. The flooding solution of FIG. 4A was normal saline solution containing 5% fatty acid-bound BSA and labeled with 2',7'-bis-(2-carboxyethyl)-5-(and -6)-carboxyfluorescein (BCECF). The model of FIG. 4B is a global permeability edema model, generated in the perfused lung by addition to the perfusate of 6 mM oleic acid to increase alveolar-capillary barrier permeability. Also in the global edema model, fluorescein is added to the perfusate for visualization. As shown by comparison of FIGS. 4A and 4B, either method generates the characteristic pattern of interspersed aerated and flooded alveoli. Light and medium gray areas, such as areas 36, indicate flooded alveoli. Darker areas, such as areas 38, indicate aerated alveoli.

In the experiments of FIGS. 5-9, 12A, 13 and 15, surface tension is determined in the local alveolar edema model in the unperfused lungs, as follows. The lung is ventilated twice between tracheal entrance pressures of 5 and 15 cmH$_2$O. Then, the lung is held at a constant transpulmonary pressure of 5 or 15 cmH$_2$O. (In the isolated lungs, transpulmonary pressure is always equal to alveolar air pressure $P_{ALV}$ and is also equal, when the lungs are held statically inflated, to tracheal entrance pressure.) Referring back to FIG. 1, $P_{LIQ\text{-}EDEM}$ is measured through a hyperosmolar saline solution-filled glass micropipette with its tip inserted into the liquid of a flooded alveolus and its shank connected to a servo-nulling pressure measurement system (Vista Electronics, Ramona, Calif.). Alveolar air pressure, $P_{ALV}$, is measured with a transducer at the trachea of the statically inflated lungs. Interfacial radius of curvature, $R_{MENISC}$, is determined by capturing the edematous alveolar meniscus in a z-stack of confocal images and mathematically fitting a sphere to the imaged interface. Surface tension, T, is determined from the Laplace relation: $P_{ALV} - P_{LIQ\text{-}EDEM} = 2T/R_{MENISC}$. Surface tension, T, is determined under control conditions and with additives included in the alveolar liquid, to determine the additives' abilities to lower surface tension. As related to FIGS. 5 through 16, discussed below, at $P_{ALV}=15$ cmH$_2$O the dyes BCECF (31 µM), fluorescein (31 µM) calcein red-orange AM (19 µM) and sulforhodamine G (SRG, 0.9 µM) do not alter surface tension whereas the dyes rhodamine WT (RWT, 1 µM) and sulforhodamine B (SRB, 0.9 µM) decrease surface tension by about 30%. Sulforhodamine B, in particular, is a promising candidate for clinical use, since it has been approved in Japan as a food dye.

FIG. 5 is a bar chart comparing the effects of dye inclusion in alveolar flooding liquid on surface tension at $P_{ALV}$ of 5 and 15 cmH$_2$O. All measurements were made in alveoli flooded with 5% fatty acid-bound BSA in normal saline. In the absence of dye (control), laser intensity and gain of the confocal microscope (Leica SP5, Buffalo Grove, Ill.) were elevated to visualize the edematous alveolar meniscus. Dyes were included at the concentrations indicated in the previous paragraph, except for fluorescein which was included at 17 µM but determined in separate experiments (data not shown) not to alter surface tension even at 31 µM. Statistics were assessed only between groups with at least n=3 replicates and are reported as mean+/−SE. At $P_{ALV}=5$ cmH$_2$O, the dye BCECF increased surface tension above control (*). No other dye altered surface tension. At $P_{ALV}=15$ cmH$_2$O, rhodamine WT decreased surface tension by 30% compared with all other groups of at least n=3 replicates (‡). Comparisons were not made to groups of n=2 replicates. However, additional replicate experiments (data not shown) demonstrated that none of the tested dyes altered surface tension at $P_{ALV}$ of 5 cmH$_2$O and none of the dyes other than SRB or RWT altered surface tension at $P_{ALV}$ of 15 cmH$_2$O. Inflation from $P_{ALV}$ of 5 to 15 cmH$_2$O caused a significant increase in surface tension (#).

Figure 6:
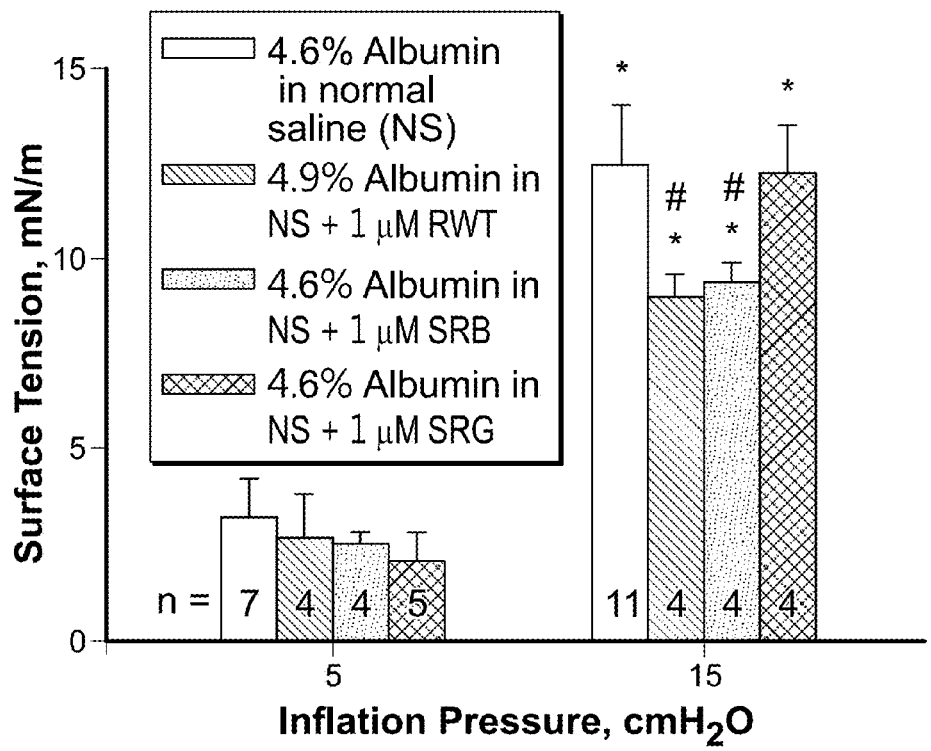
FIG. 6 is a bar chart comparing the effect of rhodamine dye inclusion on surface tension in alveoli flooded with albumin solution at two transpulmonary pressures in experiments performed to demonstrate an embodiment of the present invention.

FIG. 6 is a bar chart showing the effects of rhodamine dye inclusion on surface tension in alveoli flooded with albumin solution. The flooding solution was normal saline with about 5% fatty acid-bound BSA plus 31 µM fluorescein and rhodamine dye (i.e, RWT, SRB, or SRG) at about 1 µM (the actual concentrations of SRB and SRG were 0.9 µM). Fluorescein, which at 31 µM does not alter surface tension, was included to aid visualization of the flooding solution in the alveoli. At an alveolar pressure of 15 cmH$_2$O, including 1 µM of RWT or SRB in the flooding solution decreased meniscus radius without altering liquid phase pressure (see Table 1, below), and lowered surface tension by about 27% (see FIG. 6). Errors reported in Table 1, FIG. 6 and all subsequent FIGS. are standard deviations.

TABLE 1

| Alveolar Pressure, cmH$_2$O | Meniscus Radius, µm | | Liquid Phase Pressure, cmH$_2$O | |
|---|---|---|---|---|
| | No rhodamine dye | SRB or RWT added | No rhodamine dye | SRB or RWT added |
| 5 | 16.6 ± 4.9 (n = 43) | 14.5 ± 3.9 (n = 8) | 1.8 ± 0.6 (n = 43) | 1.6 ± 0.7 (n = 8) |
| 15 | 18.8 ± 3.1 (n = 46) | 14.6 ± 1.7 (n = 40) | 1.9 ± 1.0 (n = 46) | 2.0 ± 0.7 (n = 40) |

Figure 7:
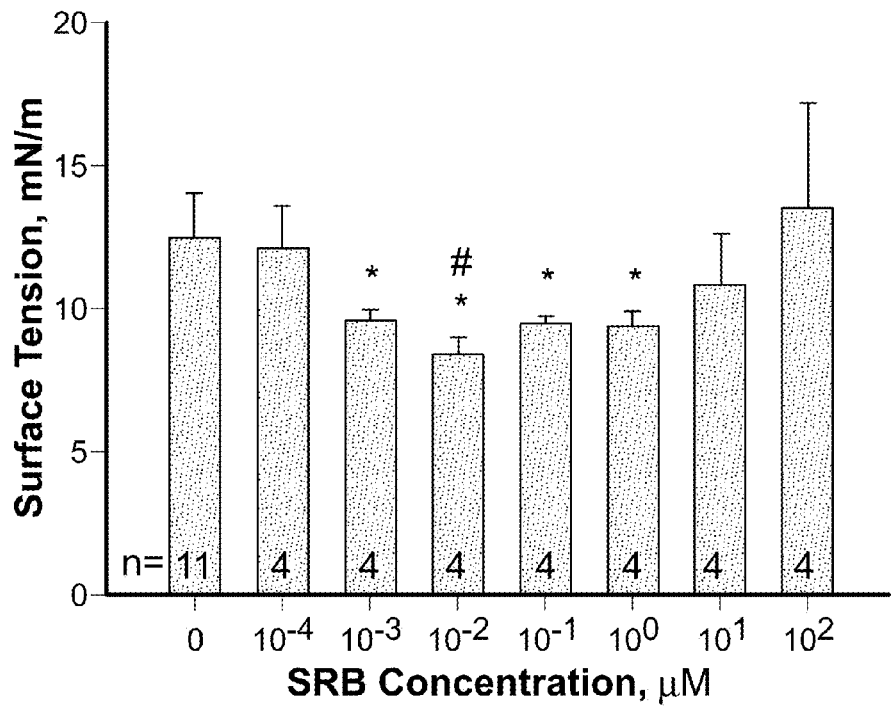
FIG. 7 is a bar chart comparing the concentration effect of a rhodamine dye on surface tension in alveoli flooded with albumin solution in experiments performed to demonstrate an embodiment of the present invention.

FIG. 7 is a bar chart showing the concentration effect of SRB on surface tension in alveoli flooded with albumin solution, at $P_{ALV}$ of 15 cmH$_2$O. The flooding solution was about 5% fatty acid-bound BSA in normal saline plus 31 µM fluorescein and SRB as specified in FIG. 7. Inclusion of 1 nM to 1 µM SRB lowered surface tension; *p<0.01 vs. no SRB and #p<0.02 vs. 1 nm and 100 nM SRB. In this concentration range, the surface tension of the flooding liquid was lowered by at least 23%. Below and above this concentration range, SRB did not significantly lower the surface tension of the flooding liquid.

Figure 8A:
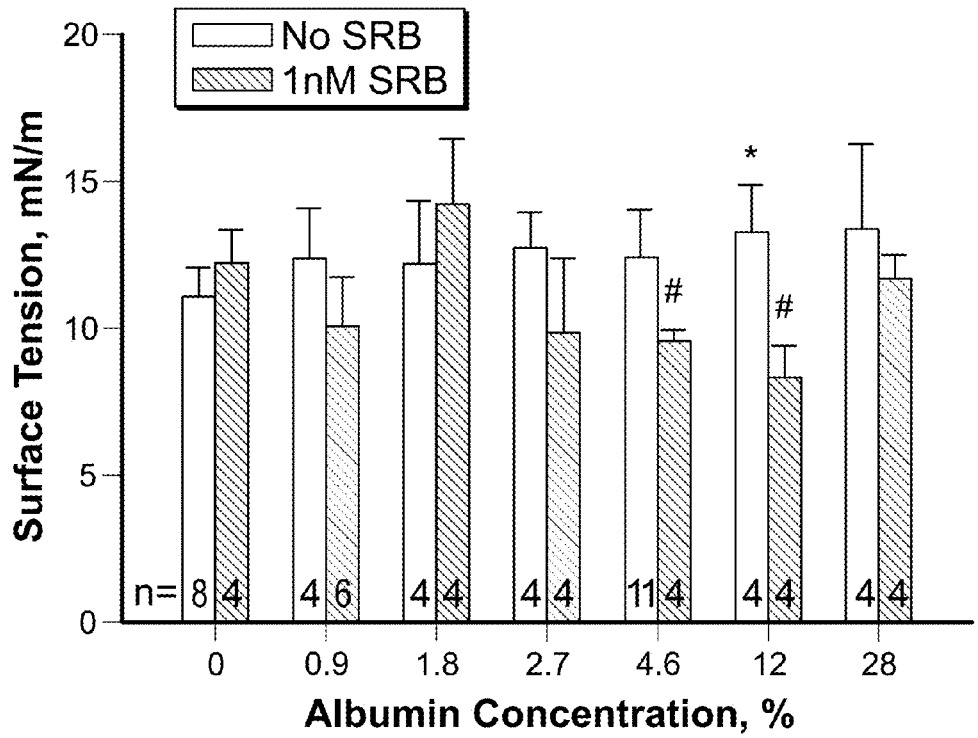
FIG. 8A is a bar chart comparing the concentration effect of albumin on surface tension in flooded alveoli, in the absence and presence of a rhodamine dye at a concentration of 1 nM in experiments performed to demonstrate an embodiment of the present invention.
Figure 8B:
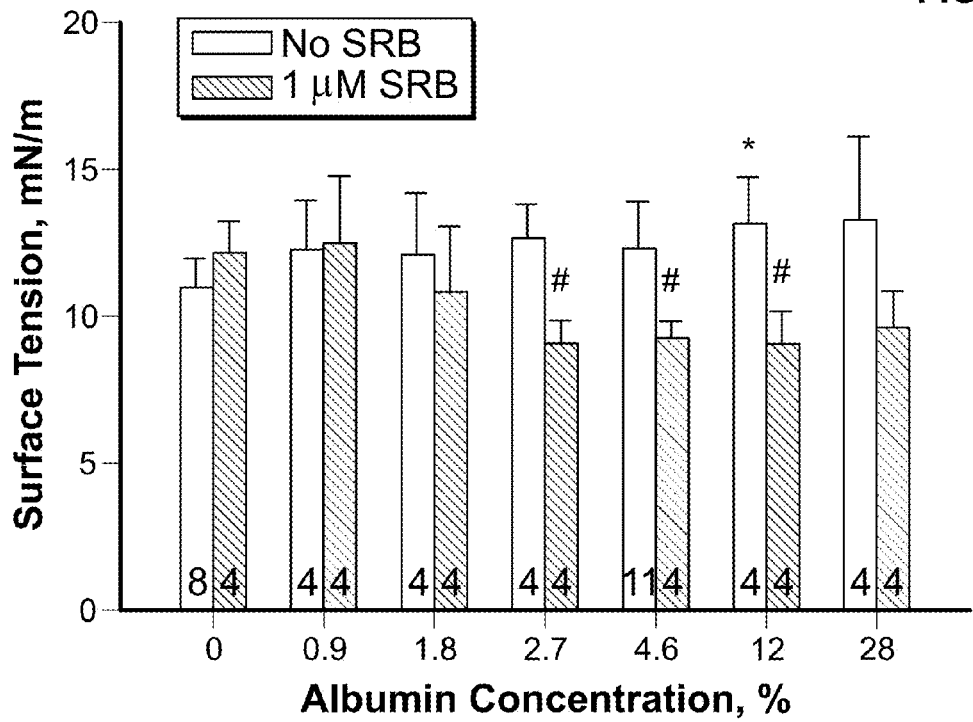
FIG. 8B is a bar chart comparing the concentration effect of albumin on surface tension in flooded alveoli, in the absence and presence of a rhodamine dye at a concentration of 1 µM in experiments performed to demonstrate an embodiment of the present invention.

To assess SRB efficacy over a range of albumin concentrations encompassing those present in ARDS, the lowest and highest effective SRB concentrations (i.e., 1 nM and 1 µM SRB) were tested in flooding solutions of normal saline containing 0% to 28% fatty acid-bound BSA and labeled with 31 µM fluorescein, at $P_{ALV}$=15 cmH$_2$O. FIGS. 8A and 8B demonstrate that SRB does not lower surface tension in the absence of albumin. In alveoli flooded with 4.6% to 12% albumin solution, both 1 nM and 1 µM SRB effectively lowered surface tension. In alveoli flooded with 2.7% albumin solution, 1 nM lost efficacy. In the absence of albumin, SRB failed to lower surface tension. It may be noted that 28% albumin, which was tested and reported in FIGS. 8A and 8B, is not a physiologic condition.

Figure 9:
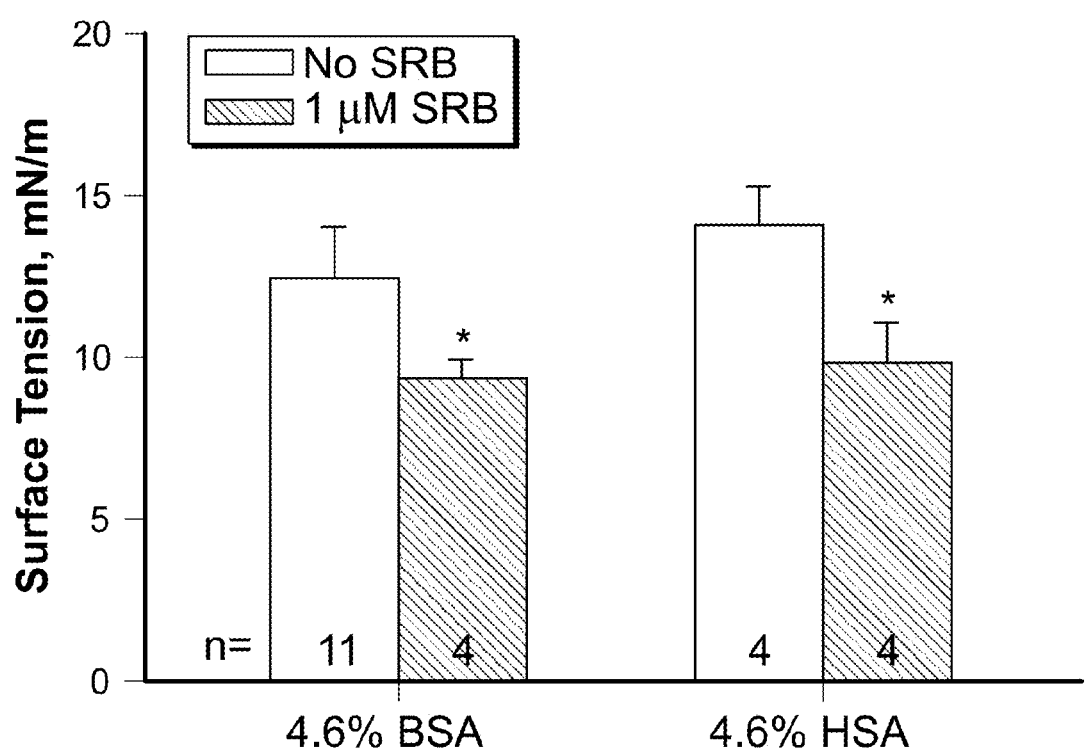
FIG. 9 is a bar chart comparing the effect of one of bovine and human serum albumin on surface tension in flooded alveoli, in the absence and presence of a rhodamine dye in experiments performed to demonstrate an embodiment of the present invention.

As shown in the preceding discussions, the inventors of the present invention have discovered that the presence of albumin facilitates the surface activity of SRB. The tests described above were conducted using BSA. Further testing was performed using human serum albumin (HSA). The flooding solution used was about 5% (more specifically, 4.6%) fatty acid-bound albumin (BSA or HSA) in normal saline plus 31 µM fluorescein, with or without 1 µM SRB. Tests were performed at $P_{ALV}$=15 cmH$_2$O. FIG. 9 shows that SRB lowers alveolar surface tension to the same degree in the presence of BSA or in the presence of HSA.

Figure 10A:
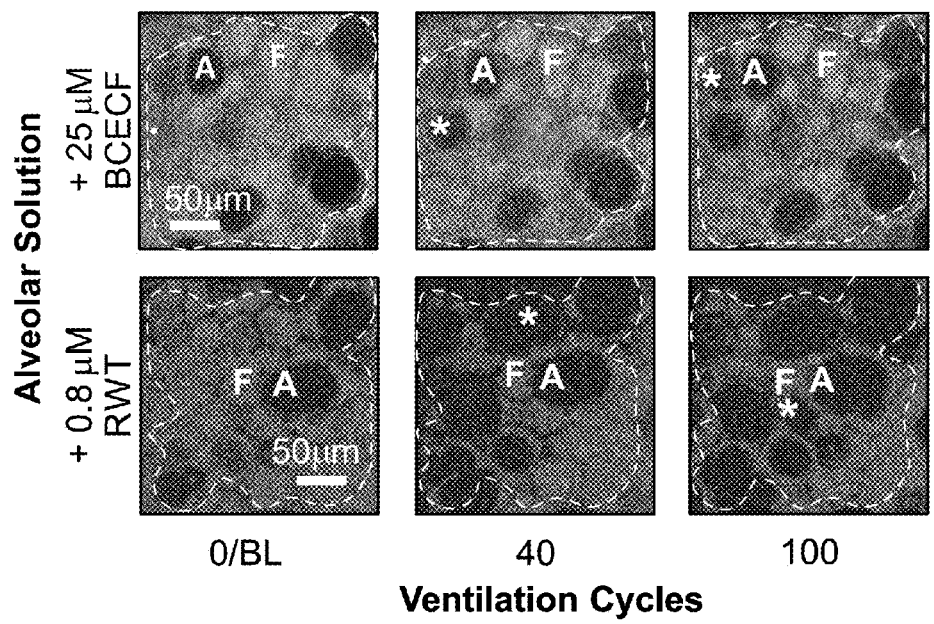
FIGS. 10A and 10B are a pairing of a set of micrographs and a graph comparing ventilation-induced alveolar clearance in a local edema model in the presence of albumin and either a rhodamine or a non-rhodamine dye in experiments performed to demonstrate an embodiment of the present invention.
Figure 10B:
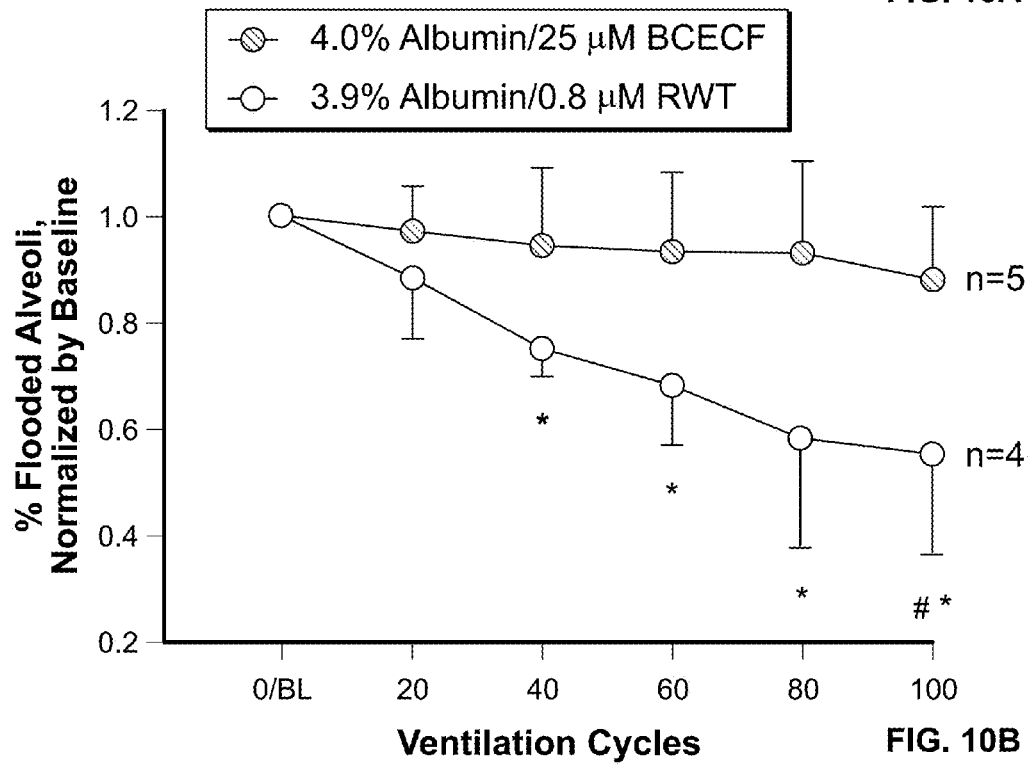
Figure 10C:
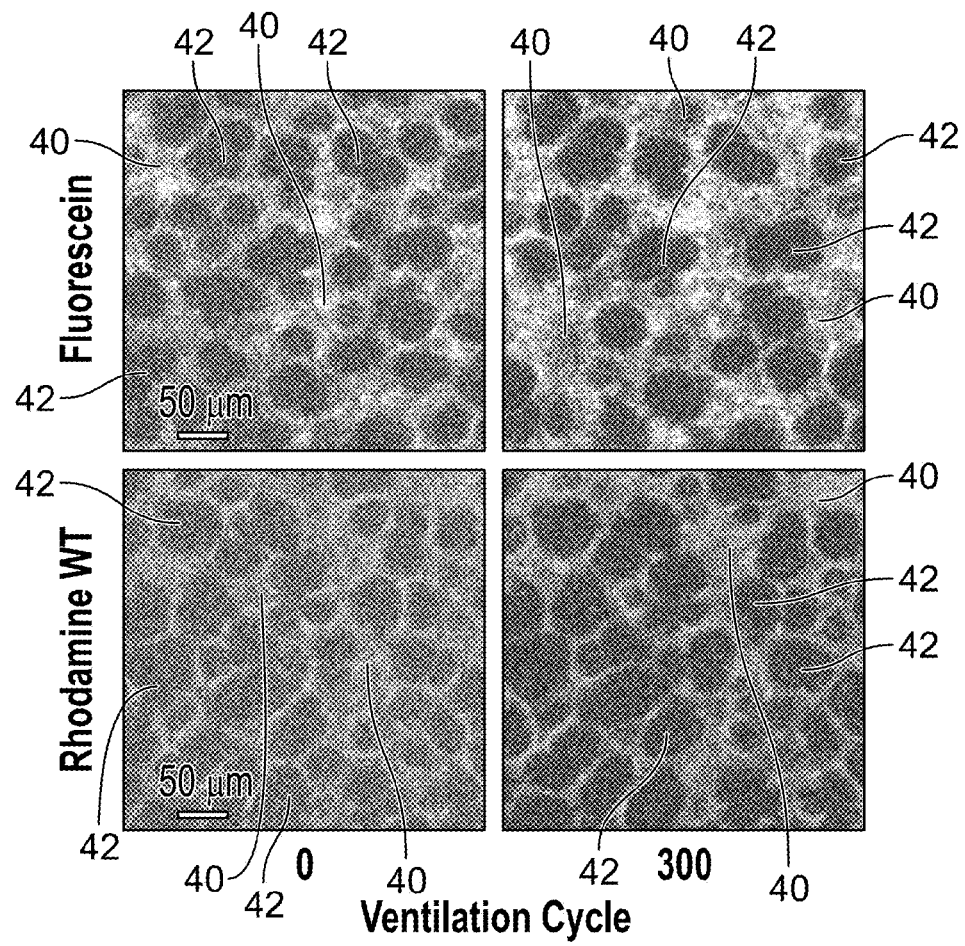
FIGS. 10C and 10D are a pairing of a set of micrographs and a graph comparing ventilation-induced alveolar clearance in a global permeability edema model in the presence of albumin and either a rhodamine or a non-rhodamine dye in experiments performed to demonstrate an embodiment of the present invention.
Figure 10D:
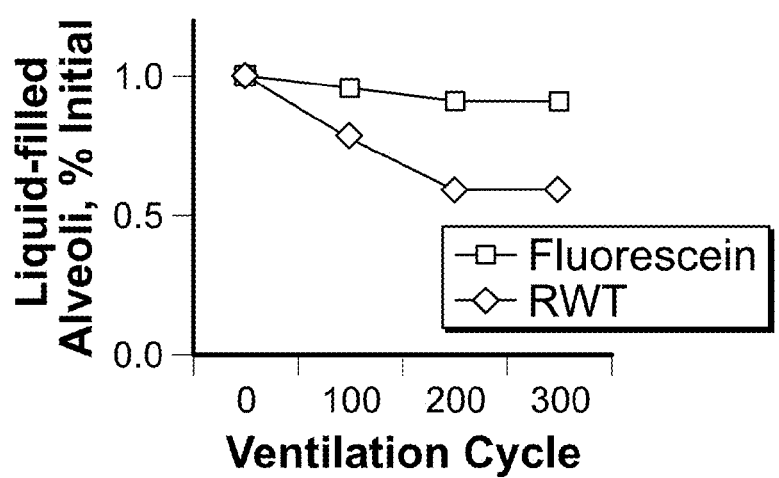

FIGS. 10A, 10B, 10C, and 10D relate to the theory of FIG. 1 and show that RWT, which lowers surface tension by about 27% and thus lowers $\Delta P_{BARRIER}$, facilitates flooded alveolar clearance whereas BCECF and fluorescein, which do not lower surface tension, do not. The micrographs and graph of FIGS. 10A and 10B show the ventilation-induced change in alveolar flooding pattern in a local edema model created by flooding surface alveoli with 4% fatty acid-bound BSA in normal saline solution including BCECF (25 µM) or RWT (0.8 µM). The micrographs and graph of FIGS. 10C and 10D show the results of the same experiment replicated in a global permeability edema model with inclusion of fluorescein (36 µM) or RWT (2 µM) in the perfusate.

In all micrographs of FIGS. 10A and 10C, exemplary flooded alveoli are shown as a lighter gray than aerated alveoli. The microphotographs of FIGS. 10A and 10C and the graph of FIGS. 10B and 10D show the effect of multiple ventilation cycles on edematous alveolar clearance. Over time during mechanical ventilation, the inclusion of RWT creates greater clearance.

Figure 11A:
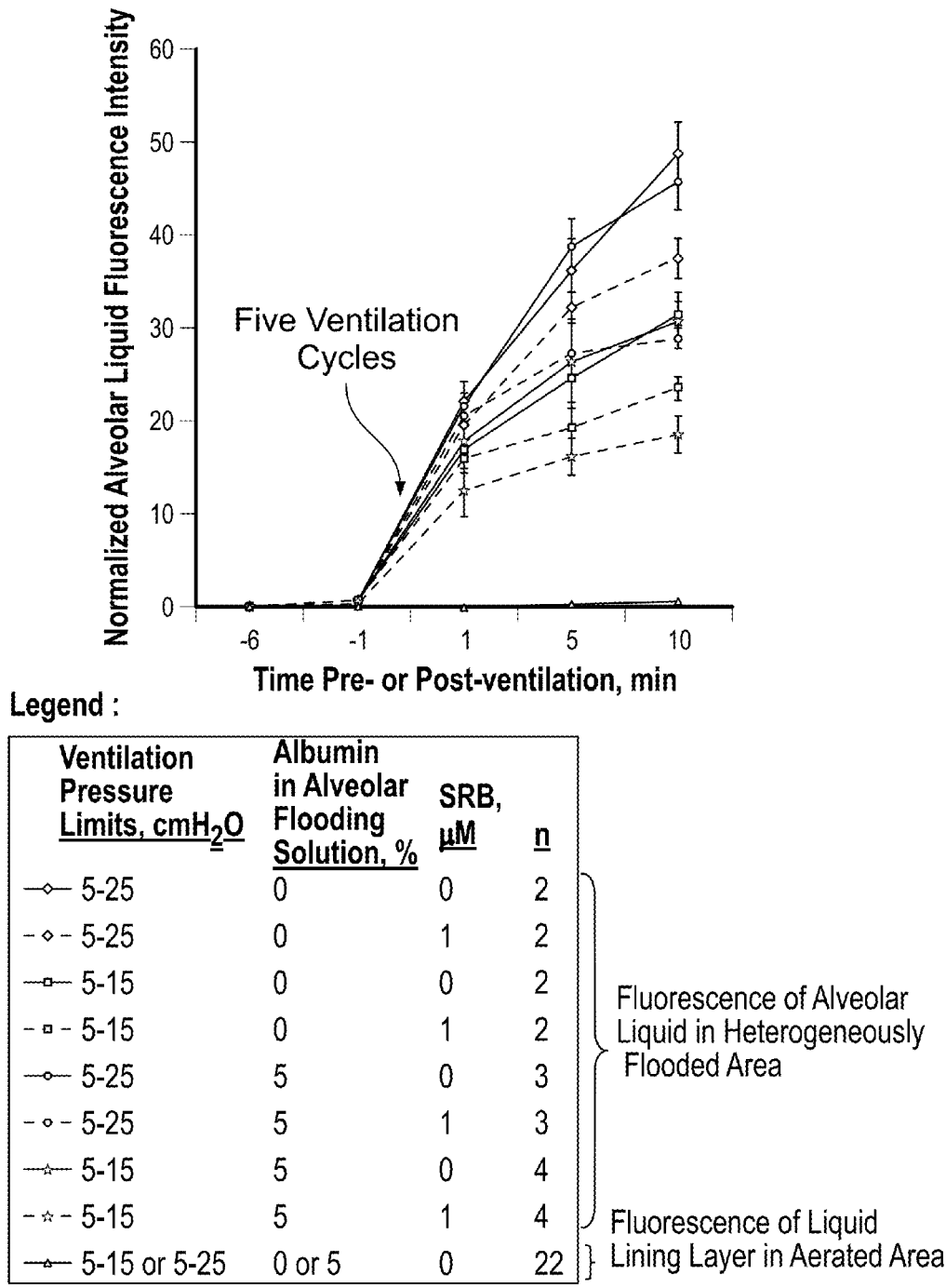
FIG. 11A is a graph of alveolar liquid fluorescence against time before and after pressure-controlled ventilation in the absence and presence of heterogeneous alveolar flooding, absence/presence of albumin and absence and presence of a rhodamine dye, in which a post-ventilation increase in alveolar liquid fluorescence indicates ventilation-induced injury, in experiments performed to demonstrate an embodiment of the present invention.

FIG. 11A shows that SRB lessens ventilation injury of the alveolar-capillary barrier in regions with discrete alveolar flooding during pressure-controlled ventilation. FIG. 11A shows data from the same injury model as discussed with respect to FIGS. 2A, 2B, and 2C, with 23 µM fluorescein included in the perfusate. By micropuncture, a non-fluorescent liquid is instilled into surface alveoli to generate a control aerated or an experimental heterogeneously flooded area. Fluorescein fluorescence in the alveolar liquid and capillary are measured at the start and end of a 5 min baseline period at constant $P_{ALV}$ of 5 cmH$_2$O. During imaging, fluorescein is excited at 488 nm, and fluorescence collected at between 493 and 535 nm. With these settings, inclusion of 1 µM SRB in the flooding solution does not alter the collected alveolar liquid fluorescence intensity. Five ventilation cycles are applied to the lungs. The lungs are then returned to a constant $P_{ALV}$ of 5 cmH$_2$O, and re-imaged at 1, 6 and 11 minutes (or sometimes, as in FIG. 11A, at 1, 5 and 10 minutes) post-ventilation. At each time point, alveolar liquid fluorescence intensity is normalized by capillary fluorescence intensity; further, the baseline normalized fluorescence intensity level is adjusted to zero. For ten minutes after the cessation of ventilation, normalized alveolar liquid fluorescence intensity rises continuously in heterogeneously flooded areas but remains constant in aerated areas. This result indicates that ventilation of regions with heterogeneous alveolar flooding injures the initially intact alveolar-capillary barrier of such regions. Further, the barrier does not reseal. Rather, the injury persists for at least ten minutes.

FIG. 11A shows that SRB lessens ventilation injury of the alveolar-capillary barrier in regions with discrete alveolar flooding during pressure-controlled ventilation. A local edema model was generated with Ringer's solution+5% 70 kD dextran (no albumin) or with normal saline+5% fatty acid-bound BSA, in the absence and presence of 1 µM SRB. The lung was ventilated between specified minimal and maximal tracheal-entrance pressures. The slope of the post-ventilation increase in normalized alveolar liquid fluorescence intensity indicates the degree of ventilation-induced injury to the alveolar-capillary barrier. In the absence of SRB, albumin inclusion does not affect degree of injury. SRB inclusion reduces injury.

Figure 11B:
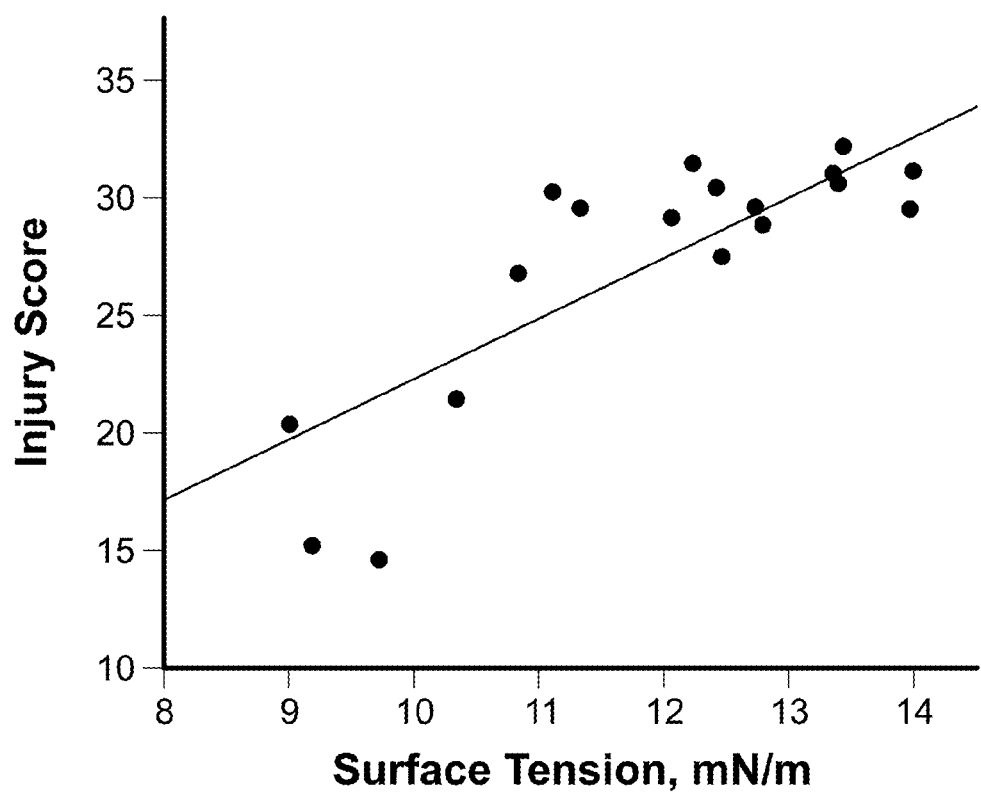
FIG. 11B is a graph comparing an injury score derived from post-ventilation alveolar liquid fluorescence data, such as those of FIG. 11A, with alveolar liquid surface tension in experiments performed to demonstrate an embodiment of the present invention.

From normalized alveolar liquid fluorescence intensity-time curves of the type shown in FIG. 11A, an 'injury score' is defined as the normalized alveolar liquid fluorescence intensity at the 11 min-post ventilation time point. As injury score correlates with the post-ventilation rate of increase in alveolar liquid fluorescence intensity, injury score indicates degree of injury to the alveolar-capillary barrier. Further, injury score correlates with surface tension of the alveolar flooding solution. FIG. 11B shows the correlation between injury score and surface tension data for solutions composed of normal saline plus 0-28% fatty acid-bound BSA, 5% fibrinogen, 5% 70 kD dextran, 10 µM NaOH or the combination of both 5% 70 kD dextran and 10 µM NaOH, all in the absence and presence of 1% of the exogenous surfactant Survanta. In one set of experiments, the solutions were labeled with 31 µM fluorescein, were instilled into surface alveoli of the isolated, non-perfused rat lung and surface tension was determined according to the methods of FIG. 5. In a separate set of experiments, the same solutions but without fluorescein were instilled into surface alveoli of the isolated, perfused rat lung; 23 µM fluorescein was added to the perfusate; the lung was ventilated with a positive end-expiratory pressure (PEEP) of 15 cmH$_2$O and a tidal volume of 6 ml/kg; and injury score was determined. Injury score was plotted against surface tension and, as surface tension did not differ significantly between groups for which surface tension was greater than 11 mN/m, a linear regression was fit to the data. As injury score correlates with surface tension, injury score is an alternative indicator of surface tension.

Figure 11C:
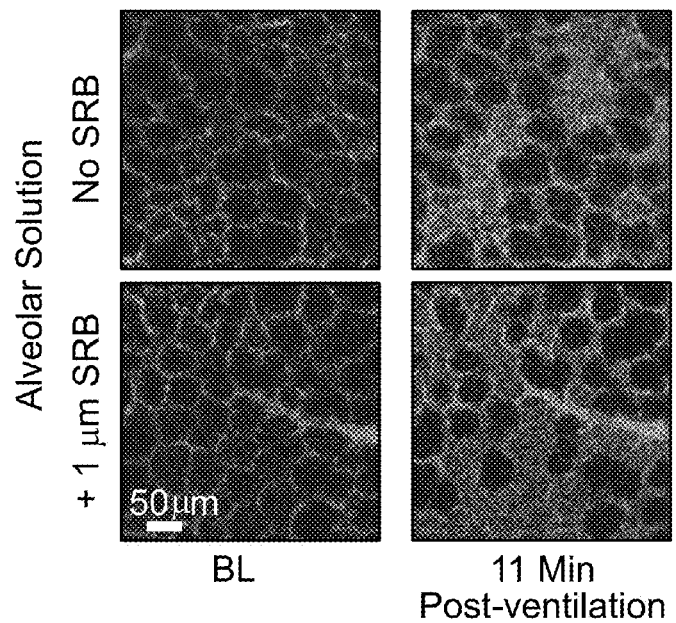
FIGS. 11C and 11D are a pairing of a set of micrographs and a graph comparing injury scores for volume controlled-ventilation in the absence and presence of heterogeneous flooding, presence of albumin and absence and presence of a rhodamine dye in experiments performed to demonstrate an embodiment of the present invention.
Figure 11D:
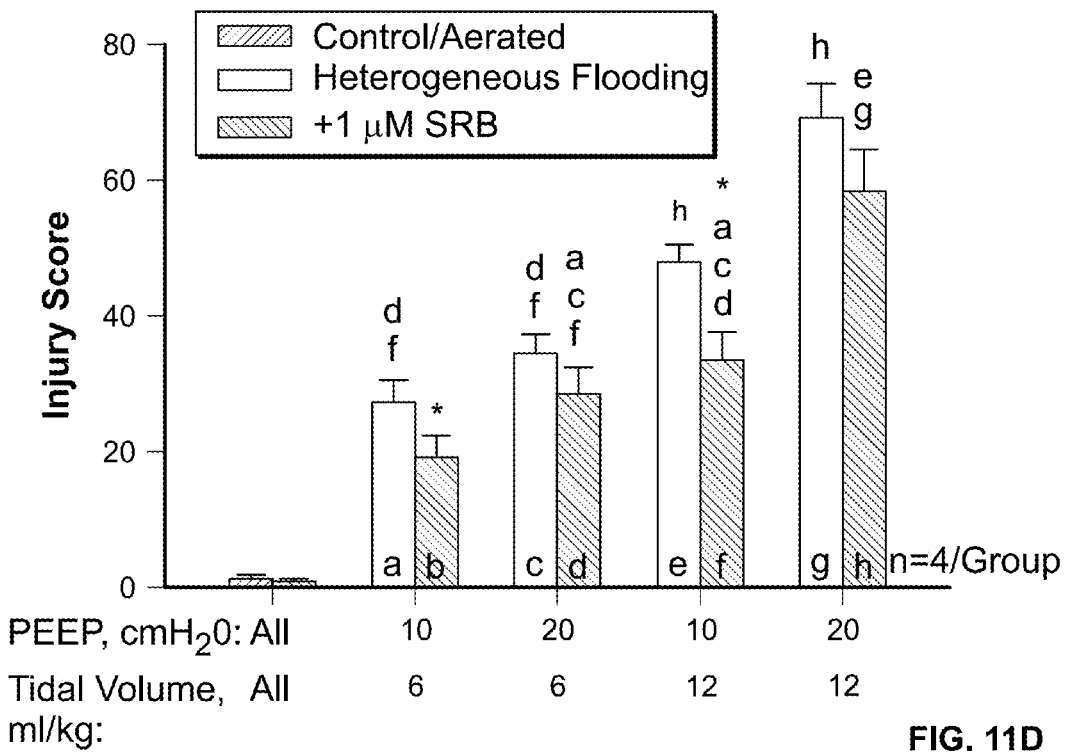

FIGS. 11C and 11D are, respectively, a microphotograph and a bar chart showing that SRB lessens ventilation injury of the alveolar-capillary barrier in regions with heterogeneous alveolar flooding by albumin solution during volume-controlled ventilation. The experiments were performed in isolated, perfused rat lungs with 23 µM fluorescein included in the perfusate. The alveolar flooding solution was 3.0% fatty acid-bound BSA in normal saline, without or with 1 µM SRB. The alveoli were flooded with the solution, and the lungs were provided with five ventilation cycles with a PEEP of 10 or 20 cmH$_2$O and a tidal volume of 6 or 12 mg/kg. Imaging was as detailed for FIG. 11A.

FIG. 11C presents images of alveolar liquid fluorescence in control and experimental areas of the perfused lung obtained at a P$_{ALV}$ of 5 cmH$_2$O at baseline (BL) before and at 11 min following five ventilation cycles with a positive end-expiratory pressure (PEEP) of 10 cmH$_2$O and a tidal volume of 12 ml/kg. FIG. 11D presents grouped injury score data for ventilation with PEEP and tidal volume as specified. The presence of discrete flooding was found to cause injury: all discrete flooding groups differ (p<0.001, statistics not shown on graph) from control, aerated groups. SRB can lessen injury: *p<0.02 vs. same ventilation settings without SRB. Higher PEEP or tidal volume increases injury: among discrete flooding groups; a group with a letter at its base differs (p<0.02) from all other groups excepting those with the same letter above their error bars. As is evident from FIG. 11D, inclusion of SRB in the alveolar flooding solution can lessen ventilation injury.

Figure 12A:
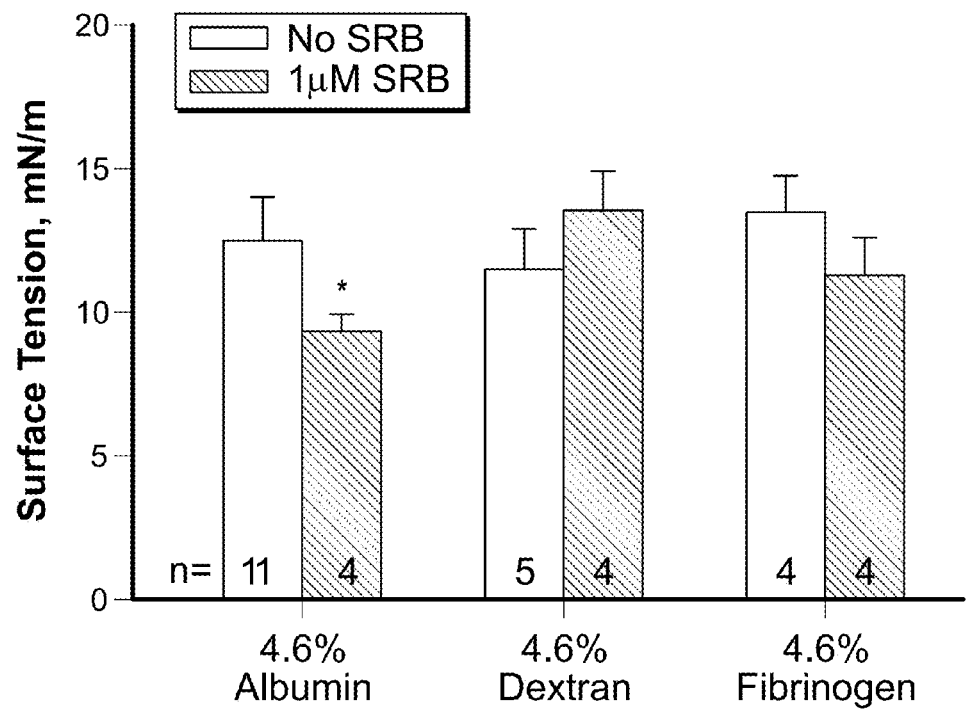
FIG. 12A is a bar chart comparing the effects of different solutes on alveolar surface tension in the absence and presence of a rhodamine dye in experiments performed to demonstrate an embodiment of the present invention.

To investigate how albumin may facilitate rhodamine activity, alternative substances were substituted for albumin, and alveolar surface tension was measured in the absence and presence of SRB. Lung regions were flooded with normal saline containing 4.6% fatty acid-bound BSA, 4.6% 70 kD dextran or 4.6% fibrinogen, plus 31 µM fluorescein. Surface tension was determined at P$_{ALV}$ of 15 cmH$_2$O. As shown in FIG. 12A, in 4.6% dextran solution, 1 µM SRB loses its efficacy. Thus, it is not the osmotic pressure of albumin solution that enables albumin to facilitate SRB surface activity. In a 4.6% fibrinogen solution, 1 µM SRB shows a tendency to lower surface tension, but does not do so significantly. Thus, only albumin facilitates SRB surface activity: *p<0.01 vs. the same solution in the absence of albumin.

Figure 12B:
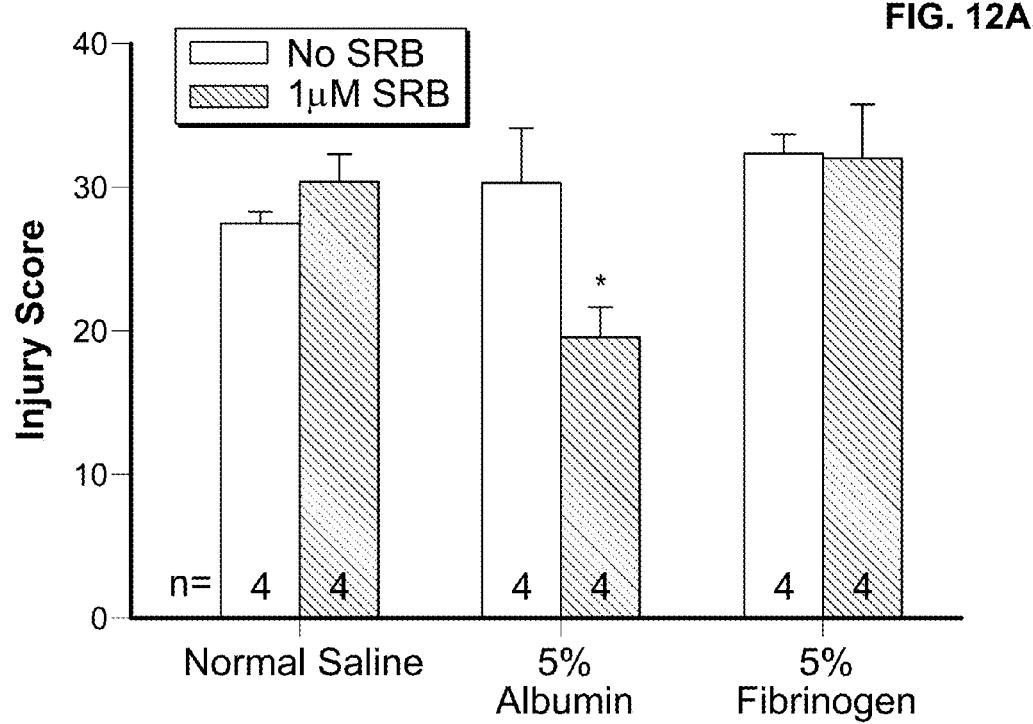
FIG. 12B is a bar chart comparing the effects of different proteins on injury score, a metric that correlates with surface tension, in the absence and presence of a rhodamine dye in experiments performed to demonstrate an embodiment of the present invention.

Additional testing supported the conclusion that albumin facilitation is necessary for SRB to lower surface tension. Since it appeared from the tests discussed with respect to FIG. 12A that SRB in fibrinogen solution might lower surface tension by an amount not detectable by the method used to determine surface tension, the investigation of SRB in fibrinogen solution was repeated using the injury assay that is, as discussed above with respect to FIG. 11B, an alternative indicator of surface tension. FIG. 12B shows the injury score for isolated, perfused lung regions with heterogeneous alveolar flooding by solutions containing 5% fatty acid-bound BSA, 5% fibrinogen, or no potentially facilitating solute (i.e., normal saline alone), in the absence and presence of 1 µM SRB. The perfusate was labeled with 23 µM fluorescein. Ventilation was performed with a PEEP of 15 cmH$_2$O and a tidal volume of 6 ml/kg. The results summarized in FIG. 12B show that albumin is necessary for SRB to lessen injury: *p<0.02 vs. same solution without SRB.

Given the different effects of albumin and fibrinogen on the surface activity of SRB, rat blood plasma was substituted for the albumin solution used in previous tests, and the effect of SRB concentration on surface tension was determined. The plasma had a total protein concentration 3.9±0.4% (n=6). The results of these tests are summarized in FIG. 13. SRB was found to be effective at lowering surface tension in the instilled plasma at concentrations of 1 nM, 10 nM, and 100 nM, but not at 1 µM.

Figure 14A:
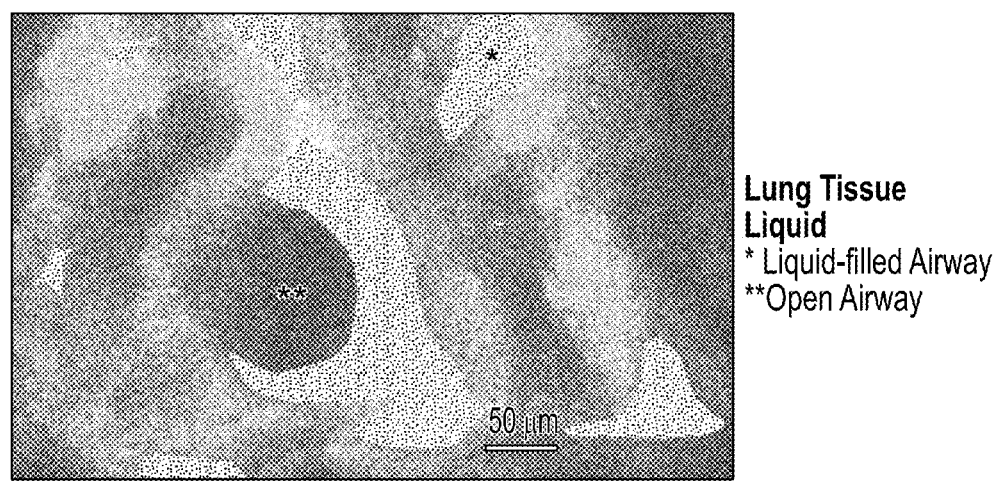
FIGS. 14A and 14B are a pairing of an enhanced micrograph and a graph depicting inflation of the immature fetal rat lung, which is deficient in native surfactant, without any tracheal instillation or following tracheal instillation of solutions lacking albumin, where fetal lung opening pressure correlates with surface tension of the natural or instilled tracheal liquid, in experiments performed to demonstrate an embodiment of the present invention.
Figure 14B:
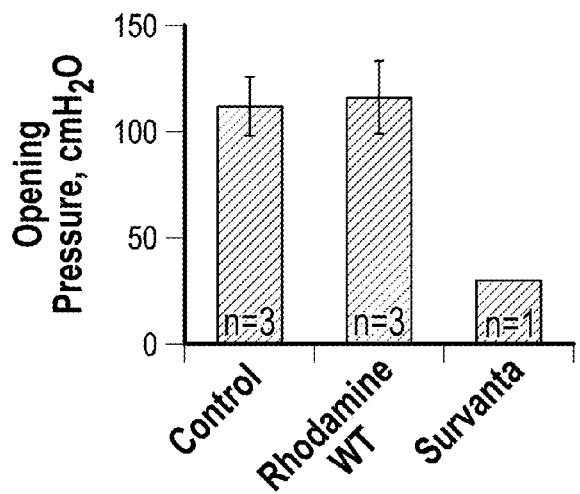

FIGS. 14A and 14B are a pairing of an enhanced micrograph and a graph depicting inflation of the immature (embryonic day 18) fetal rat lung deficient in native surfactant. The micrograph is a confocal image of the inflated fetal lung. Air is shown in dark gray, epithelial cells are shown in light gray, and airway liquid is shown with light stippling. FIG. 14B presents initial lung opening pressure data for a control group, in which no liquid was instilled in the trachea, and for experimental groups, in which about 5 µL of (i) rhodamine WT in normal saline or (ii) Survanta was instilled in the trachea before lung inflation. In no group was albumin included in the solution instilled in the trachea. The opening pressure of the fetal lung is directly related to the surface tension of the solution in the trachea, whether native fetal lung liquid or instilled solution. These results indicate that RWT is not directly surface active on its own (i.e., in the absence of both lung surfactant and albumin).

To investigate whether SRB is directly surface active in albumin solution, the surface tensions of solutions containing albumin and/or SRB were determined in vitro according to the following method. A 3 µL drop of normal saline that included 31 µM fluorescein and additional solutes as specified was placed on a steel plate, and the pressure within the test drop was measured through a hyperosmolar saline-filled glass micropipette with its tip immersed in the drop and its shank connected to a servo-nulling pressure-measurement system. The pipette and servo system were of the same type as discussed with respect to FIG. 5. With the pipette still in the liquid drop, the drop was imaged by confocal microscopy with an ×10 (0.3 N.A.) air objective over a total imaging time of about one minute. A sphere was mathematically fit to the air-liquid interface to determine the interfacial radius of the drop. The surface tension of the liquid drop was calculated according to the Laplace relation.

Figure 15:
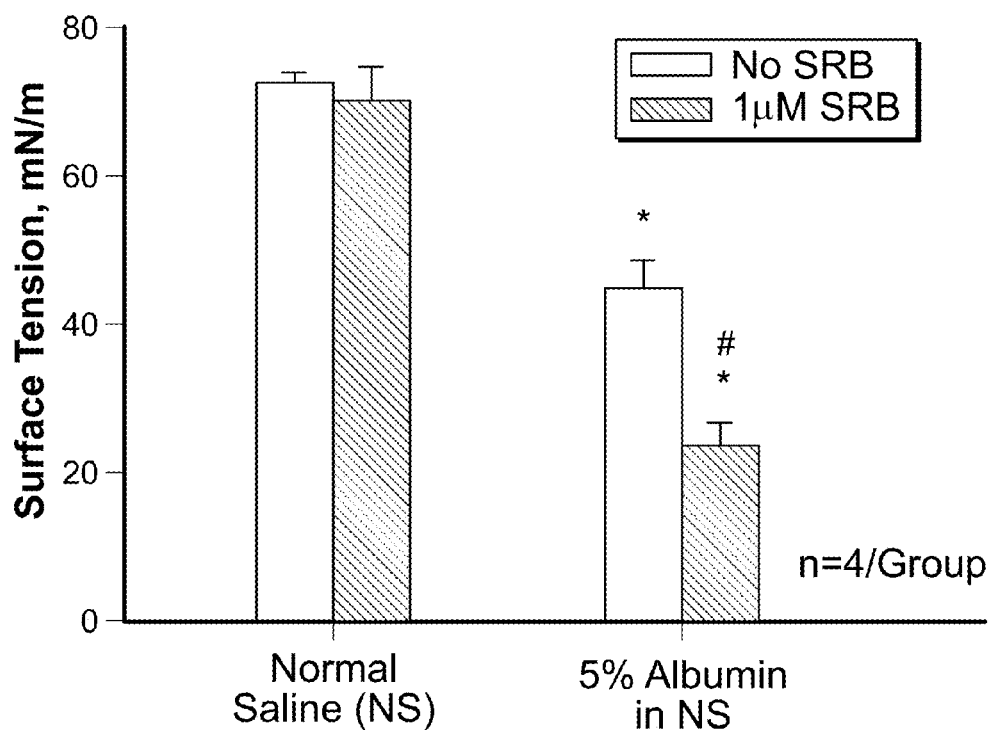
FIG. 15 is a bar chart comparing the effects on in vitro normal saline drop surface tension of rhodamine dye alone, albumin alone, or rhodamine dye and albumin together in experiments performed to demonstrate an embodiment of the present invention.

The in vitro tests, summarized in FIG. 15, showed that that, as expected, the surface tension of a drop of normal saline was about 73 mN/m, and was unaltered by addition of 1 µM SRB. Also as expected, the surface tension of 5% fatty acid-bound BSA in normal saline was about 45 mN/m. Subsequent addition of 1 µM SRB to 5% fatty acid-bound BSA solution reduced surface tension to about 24 mN/m. Based on the replicate tests (n=4), albumin lowered surface tension: *p<0.001 vs. normal saline solution without or with SRB. SRB further lowered surface tension: #p<0.001 vs. albumin solution without SRB. It therefore appears that the combination of SRB and albumin is directly surface active.

The additive experiments discussed above with respect to FIGS. 5 through 15 demonstrate that SRB has the ability to lessen direct ventilation injury and that the protection is facilitated by the presence of albumin in the alveolar flooding liquid (see FIGS. 8A, 8B, and 8C). Further, the ability of RWT to promote flooded alveolar clearance was tested. Edema models were generated with either BCECF or RWT included in the flooding liquid (local edema model) or with fluorescein or RTW included in the perfusate (global edema model). More alveoli were found to clear after ventilation when RWT was present than when either BCECF or fluorescein were present (see FIG. 10). Given that SRB lowers surface tension to the same degree as RWT (see FIG. 5) and provides direct protection against ventilation injury (see FIGS. 11A and 11D), SRB is expected to promote alveolar clearance to the same degree as RWT.

Without being bound by theory, it is believed that SRB and RWT, incorporated into albumin-containing alveolar flooding liquid of the lungs as in embodiments of the present invention, lower surface tension, but it is not known whether they do so directly or by indirectly promoting adsorption to the interface of native lung surfactant, which is present in the lungs in vivo and in isolated rat lungs in situ. To rule out direct surface activity of SRB/RWT, the inventor used a fetal rat lung model deficient in surfactant (see FIGS. 14A and 14B). The pressure required initially to inflate the completely flooded fetal lungs is proportional to the surface tension of the liquid in the trachea. Tracheal instillation of exogenous surfactant (e.g., Survanta) lowers the opening pressure, as well as subsequent ventilation pressures. Instillation of RWT alone, without surfactant or albumin, failed to decrease opening pressure, thus confirming that RWT is not directly surface active.

The following discussion presents a number of observations that should be taken into account when implementing embodiments of the present invention.

Effective Albumin Concentration Range.

SRB was found to lower surface tension when instilled in combination with 2.7% to 12% albumin solution. In ARDS, edema liquid albumin concentration averages about 3%. Thus, the albumin concentration range in which SRB is effective overlaps with the albumin concentration range present in clinical ARDS. To ensure that the albumin concentration in the alveolar liquid is sufficient for facilitating SRB, It might be necessary to administer supplemental albumin (albumin would most likely be administered intravascularly, but could be administered via the trachea) at the same time as SRB.

Figure 13:
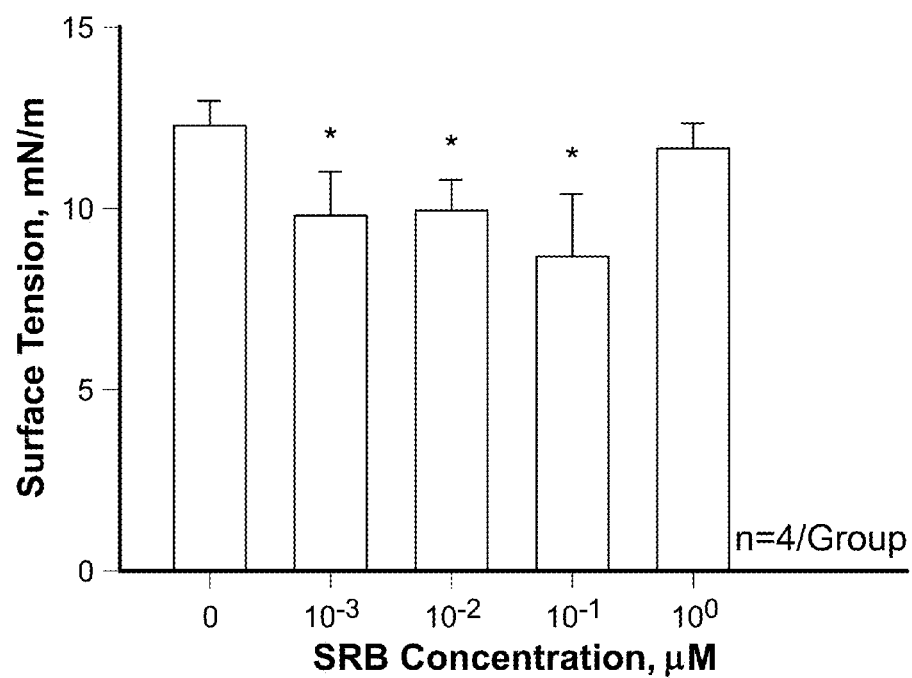
FIG. 13 is a bar chart comparing the concentration effect of a rhodamine dye on surface tension in alveoli flooded with blood plasma in experiments performed to demonstrate an embodiment of the present invention.

Further, SRB at 1 µM was found to lower surface tension in combination with 2.7% albumin solution, but not with rat blood plasma (FIGS. 8B, 8C, and 13). As total protein concentration in the rat plasma that was tested was 3.9%, and albumin accounts for about 52% of all proteins in rat plasma, the albumin concentration in rat plasma may be close to that of a 1.8% albumin solution, in which SRB was found to be ineffective (FIGS. 8B and 8C). In contrast, while 1 nM SRB was not found to be effective in 1.8 or 2.7% albumin solution, SRB concentrations in the range of 1 to 100 nM were found to be effective in rat plasma. Without being bound by theory, it may be that there are yet-to-be-identified components of plasma that facilitate the reduction of surface tension at these lower SRB concentrations.

Rhodamine Dye-Albumin Interaction.

As discussed above, SRB and RWT require the presence of albumin, or potentially of an alternative facilitating solute such as might be present in plasma, in order to lower surface tension, whether in the absence of lung surfactant in vitro or in the presence of lung surfactant in situ in the isolated rat lung. SRB is known to bind to albumin. SRB is also known to interact with and increase the surface activity of the surfactant sodium dodecyl sulfate (SDS), suggesting that SRB might interact with lung surfactant phospholipids.

Amphiphilic SRB is, on its own, surface active. Computational modeling done by others suggest that the xanthene rings of SRB, despite the iminium cation that they support, constitute the hydrophobic moiety of SRB and that, when SRB adsorbs, the xanthene rings align with the interface. However SRB on its own is only surface active at greater than 1.3 mM, a concentration far greater than the 1 nM to 1 µM concentration range in which we found SRB, in conjunction with albumin, surface active. At the SRB concentrations that we tested, SRB on its own is not expected to alter surface tension. Accordingly, as discussed herein, addition of 1 µM SRB to a saline drop in vitro does not alter the surface tension of the drop (FIG. 15).

SRB binds by hydrophobic interaction to the Sudlow site I of fatty acid-free albumin at a stoichiometry of about 1:1, with the hydrophobic xanthene rings of SRB likely situated in the albumin binding cavity. In the tests discussed in the present application, SRB at concentrations up to 1 µM were combined with 5% (0.7 mM) fatty acid-bound albumin. Given the low SRB concentration relative to that of albumin, it is likely that a significant fraction of the SRB was bound to albumin. How the presence of fatty acids affects the stoichiometry of SRB-albumin binding, however, might be directly tested, as it is possible that the quantity of bound fatty acids affects the efficacy of SRB in the presence of albumin.

In the in vitro experiments discussed in the present application, it was found that the surface tension of a solution containing both SRB and albumin was significantly lower, 24 mN/m, than that of a solution containing SRB or albumin alone (FIG. 15). As a comparison, adsorption of lung surfactant to a stationary interface lowers surface tension to 26 mN/m. It is possible that the surface tension-lowering effect of SRB in situ in the lungs is attributable to direct SRB-albumin surface activity.

Alternatively, SRB and albumin may interact with lung surfactant in situ in the isolated lungs. SRB, which at a given concentration is less surface active than SDS, is known to enhance the surface activity of SDS. Computational modeling done by others suggests that SRB inserts into the outer layer of SDS micelles—the xanthene rings of SRB, again, likely most embedded. However, the SRB concentration at which this facilitation of SDS has been shown to occur, 9 mM, is far greater than the SRB concentrations disclosed herein. Further, whether SRB/albumin affects alveolar epithelial type II cell secretion or reuptake of surfactant has not been investigated.

How SRB, albumin and lung surfactant interact is not known. As the xanthene rings of SRB embed in both albumin and in SDS micelles, it is unlikely that SRB links albumin to surfactant. Without being bound by theory, it is likely that SRB and albumin are already bound when the solution containing SRB and albumin is instilled into the lungs. Whether lung surfactant interacts with SRB or albumin, perhaps competing for SRB in a fashion that alters surface tension, remains to be determined.

SRB/RWT Chemistry.

SRB and RWT have a surface tension lowering capability that the dyes fluorescein, BCECF, calcein red-orange AM, and even sulforhodamine G lack. SRB and RWT also have an unique aspect to their chemical structure. While all six of the above dyes are aromatic fluorescent compounds, and all but calcein red-orange AM have anionic groups, SRB and RWT are distinguished by the additional presence of an iminium cation ($R_1=N^+$—$R_2R_3$). It would thus be expected that other molecules with structures similar to that of SRB and RWT would likewise promote surfactant adsorption and reduce surface tension when instilled into the lungs according to embodiments of the present invention. Aromatic dissociated salt anions possessing one or more carboxyl, hydroxyl, or equivalent groups plus one or more cationic groups may also act equivalently to SRB and RWT. Additives other than aromatic salts (e.g., zwitterionic salts) may also be effective in reducing surface tension when instilled into the lung.

RWT and SRB Toxicity.

Sulforhodamine B is approved as a food dye in Japan, and both SRB and RWT are used as ground water tracers. There is an extensive literature on the toxicity of these dyes. A brief survey of this literature reveals that most toxicity studies have been performed using dye formulations of unknown purity. The exception, summarized at the end of this section, is a series of SRB toxicity tests performed by a European Commission committee using high purity SRB.

Rhodamine WT has an $LD_{50}$ of 430 mg/kg (5, 14). In limited in vivo testing of RWT, administration of 25-80% of the $LD_{50}$ over 1-5 days did not cause histopathologic changes, increase the rate of micronuclei generation or increase the rate of occurrence of sperm abnormalities. Results of in vitro tests of RWT genotoxicity/mutagenicity, however, have been mixed. Rhodamine WT tested negative for genotoxicity at 4 mM by mammalian cell sister chromatid exchange and at 12 mM by mammalian cell chromosome aberration test. Yet RWT tested positive at about 2 to about 10 μM and 4 mM by Ames test and at about 2 to about 10 μM by mammalian cell chromosome aberration test. The purity of the dyes used in the above studies is not known and it is possible that purified RWT would test negative for genotoxicity. Based on the existing literature, however, RWT does not appear suitable for use as a clinical agent.

SRB of unknown purity tested negative for genotoxicity at about 2 μM to about 10 μM by Ames test; at 10 μM and 1.7 mM by Rec assay; and at about 2 μM to about 10 μM by mammalian cell chromosome aberration test. The only study in which SRB tested positive for genotoxicity is one in which the tested SRB concentration is not stated. In a series of tests on the cytotoxicity of Japanese food dyes, toxicity of SRB at 1 to 2 mM, which is greater than 1000 times the highest concentration at which the present application shows SRB to lower surface tension, was not found to be of cytotoxic concern, except for the detection of low level toxicity in cultured fetal rat cells at day four after plating that decreased by day seven. Further, following administration of 2000 mg/kg SRB to pregnant rats, there was no evidence of DNA damage in cells biopsied from dams or embryos.

A 2008 report by the Scientific Committee on Consumer Products of the European Commission presents SRB toxicity data from tests in which dye formulations of generally high purity were used. The $LD_{50}$ for SRB (unknown purity) was found to exceed 1000 mg/kg. Administration of 1000 mg/kg/day of greater than 99% purity SRB for 13 weeks to mature rats produced no observable adverse effects. Administration of 1000 mg/kg/day of greater than 99% purity SRB for 12 days to pregnant rats produced no observable adverse effects in dams or fetuses. One-time administration of 2000 mg/kg of greater than 90% purity SRB to mice did not increase the rate of generation of micronuclei. A diet of 5% of greater than 99% purity SRB over two years was not carcinogenic in rats. Finally, SRB of greater than 99% purity tested negative for genotoxicity at 9 μmol/plate by Ames test and at 9 mM by mammalian cell chromosome aberration test. SRB appears to be a suitable candidate for clinical administration.

Potential Therapeutic Applications.

As disclosed in the present application, SRB concentrations of 1 nM to 100 nM effectively lower surface tension in both 4.6% albumin solution and in rat plasma (FIGS. 7 and 13). Due to post-microinjection diffusive solute efflux from the alveolus in the time required to determine the surface tension, the actual SRB concentration tested may be less than the concentration instilled. Thus, an actual alveolar SRB concentration of 1 nM to 10 nM would likely be an appropriate target clinical concentration.

In clinical applications of embodiments of the present invention, SRB, without or with supplemental albumin, could be delivered to the alveolus via the trachea or the vasculature. If delivered via the trachea, mechanical ventilation and diffusion should both propel SRB, or SRB and albumin, toward the alveoli. Concurrent tracheal instillation of exogenous surfactant might enhance SRB and/or albumin delivery by generating Marangoni flows toward the alveoli. It is also possible that SRB, without or with albumin or surfactant, could be instilled in more distal airway(s), e.g. via bronchoscope. SRB, without or with albumin, might be instilled in a concentrated bolus in the trachea or airways such that, once distributed throughout the lung edema liquid, SRB and albumin concentrations would be within the appropriate ranges for lowering surface tension.

An alternative route of SRB delivery, without or with supplemental albumin, would be via the vasculature. In ARDS, alveolar-capillary barrier permeability is sufficiently elevated to allow albumin entrance into the alveolus thus should also allow free- or albumin-bound SRB to diffuse out of the vasculature into the alveolar liquid phase. SRB delivery via the vasculature, which must also be investigated, holds potential as a new therapy for the treatment of ARDS.

Neonatal Respiratory Distress Syndrome.

A surface tension-lowering additive has potential application in the treatment neonatal RDS. Babies born prematurely before producing their own surfactant are treated by tracheal instillation of exogenous surfactant. Due to patchy aeration and/or surfactant delivery throughout the lungs of such premature infants, mechanical ventilation injures the alveolar-capillary barrier and albumin leaks from the blood into the lung liquid. Thus administration of an albumin-dependent surface tension lowering agent to the alveolar liquid in such premature infants has the potential to ameliorate neonatal RDS. As in ARDS, a surface tension lowering additive could be administered to neonates via the trachea, without or with exogenous surfactant and without or with supplemental albumin, or could be administered via the vasculatures, without or with supplemental albumin. Use of a surface tension lowering additive could improve treatment for neonatal RDS and/or lower the cost of treating neonatal RDS by decreasing the required exogenous surfactant dosage. In babies delivered just as they are beginning to produce native surfactant, SRB, RWT or equivalent might act as a bridge support by compensating for the low levels of native surfactant, or potentially enhancing the activity of the low levels of native surfactant, until more surfactant is produced.

Industrial Use of Additives.

Industrial surfactants are generally simpler in structure than pulmonary surfactant. Industrial surfactants are generally mono-molecular and may be positively charged, uncharged or negatively charged. Additives such as those discussed above might, by extension, be combined with albumin or an alternative facilitating solute and the combination might be used as an industrial surfactant or might be used in combination with an industrial surfactant to enhance surfactant adsorption and surface tension reduction.

2. Active Deflation During Mechanical Ventilation

According to embodiments of the present invention, sudden deflation of the lung will, effectively, catapult edema liquid out of the alveoli in which it is trapped. As discussed further herein, the effectiveness of this embodiment of the present invention has been demonstrated in the local alveolar edema model and global permeability edema model in the isolated, perfused rat lung.

Figure 16:
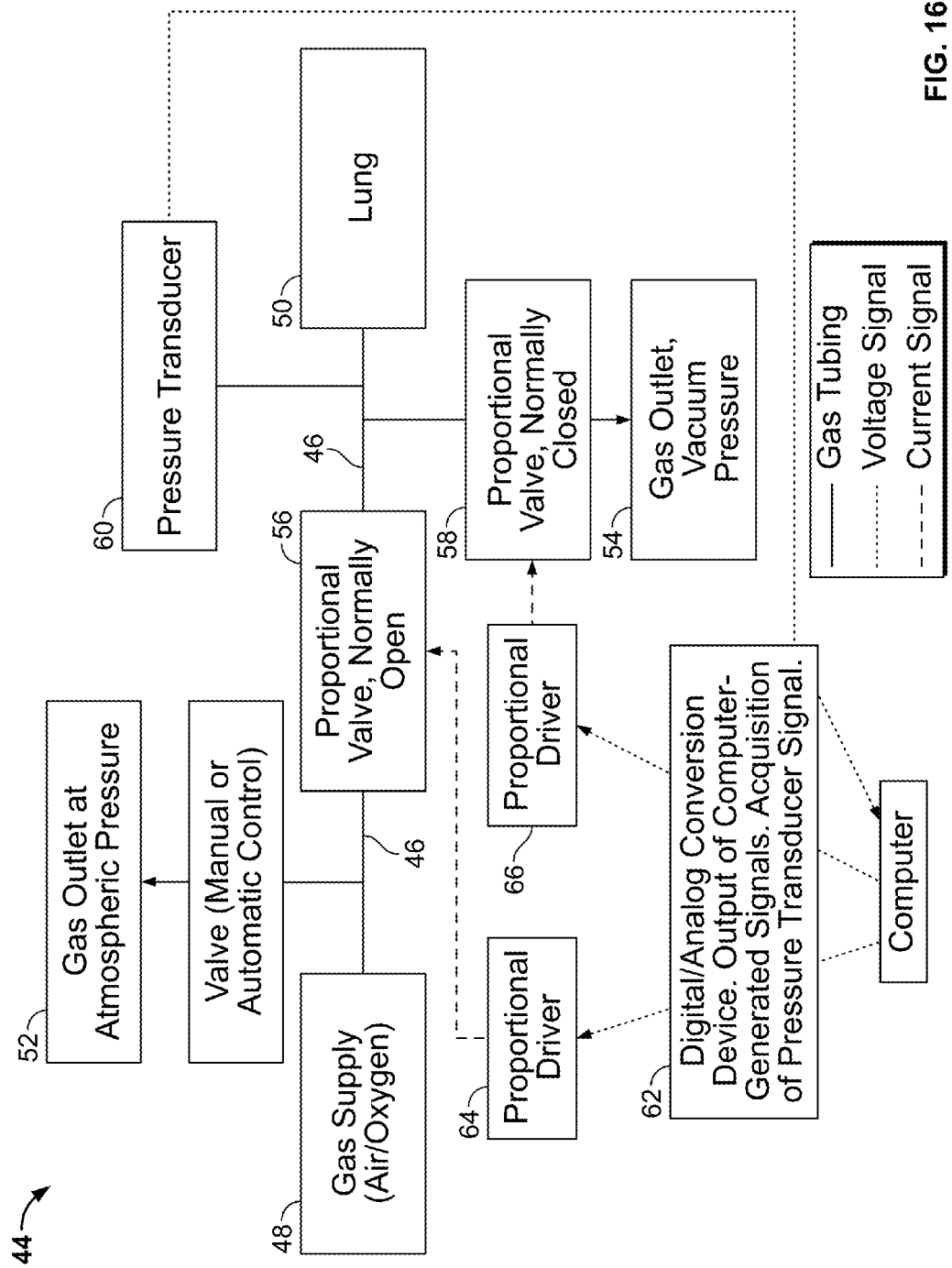
FIG. 16 is a schematic block diagram of an apparatus for the generation of custom ventilation pressure waveforms, according to an embodiment of the present invention.

FIG. 16 is a schematic block diagram of an apparatus 44 for the generation of custom ventilation pressure waveforms, according to an embodiment of the present invention. A tubing line 46 links the ventilation gas source 48 to the lung 50. Along the tubing line 46 are two outlets 52, 54, one outlet 52 opening to atmospheric pressure, the other outlet 54 opening to vacuum pressure. Located between the two outlets 52, 54 is a normally-open proportional valve 56, and along outlet 54 is a normally-closed proportional valve 58. Between outlet 54 and the lung 50, a pressure transducer 60 measures and indicates pressure in the tubing line 46. In some embodiments of the present invention, the pressure transducer 60 is proximate the end of the tubing line 46 where it is fluidly connected to the lung 50, such that the pressure measured by the pressure transducer 60 is substantially the same as the pressure at the entrance to the trachea (not shown). A custom Labview® program acquires pressure data from the transducer 60 and, in an open-loop fashion, provides voltage signals that control the proportional valves via a digital/analog conversion device 62 and appropriate proportional drivers 64, 66. The development of suitable computer programs and selection of conversion devices 62 and drivers 64, 66 are within the ability of those having ordinary skill in the relevant art. In some embodiments of the present invention, the first outlet 52 is omitted, and the normally-open proportional valve 56 is placed in the tubing line 46 between the end of the tubing line 46 that receives gas from the ventilation gas source 48 and the outlet 54.

In an embodiment of the present invention, the lung 50 is inflated to peak volume, and abrupt deflation is effected by simultaneous application of step voltage increases to valves 56, 58, causing the valves 56, 58 suddenly to close and open, respectively. Valve 58 remains open until the pressure measured in the tubing 46 has decreased to a targeted pressure, which may be the desired positive end-expiratory pressure, at which time voltage to valve 58 is returned to zero, causing valve 58 to close. At the subsequent, specified time for initiation of inflation, voltage to valve 56 is reduced exponentially such that valve 56 opens gradually and ventilation gas passes through valve 56 to inflate the lung 50. Thus, the lung 50 is actively deflated while maintaining a positive pressure at the lung 50. This maintenance of positive pressure at the lung 50 during mechanical deflation of the lung 50 is one of the characteristics of the present invention that distinguishes it over methods existing in the prior art.

The apparatus 44 of FIG. 16 is useful for generating a ventilation pressure waveform with gentle deflation (sinusoidal) when outlet 54 is open to the atmosphere and valve 58 is opened gradually during deflation, or with sudden, passive deflation (sawtooth) with an exponential increase in pressure and a sudden, passive decrease in pressure when outlet 54 is open to the atmosphere and valve 58 is opened suddenly at the start of deflation. When outlet 54 is attached to a vacuum source and valve 58 is opened suddenly at the start of deflation (accelerated sawtooth), as in embodiments of the present invention, the deceleration is sudden and accelerated.

Figure 17A:
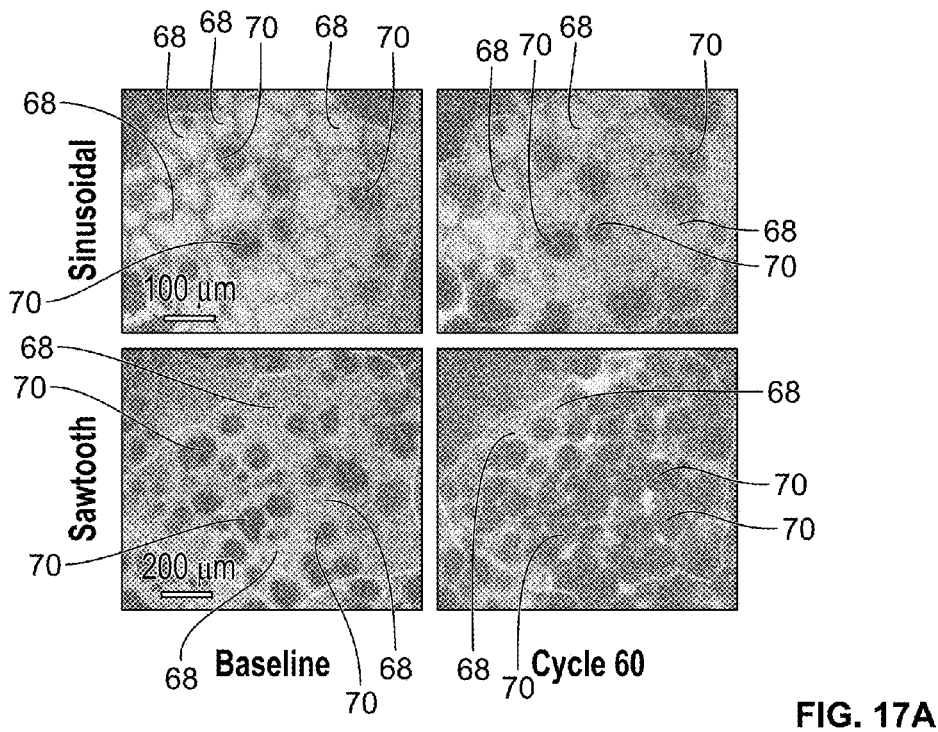
FIGS. 17A and 17B are a pairing of a set of micrographs and a graph comparing clearance of alveoli in a local edema model by ventilation using a sinusoidal pressure waveform and ventilation using a sawtooth waveform, according to embodiments of the present invention.
Figure 17B:
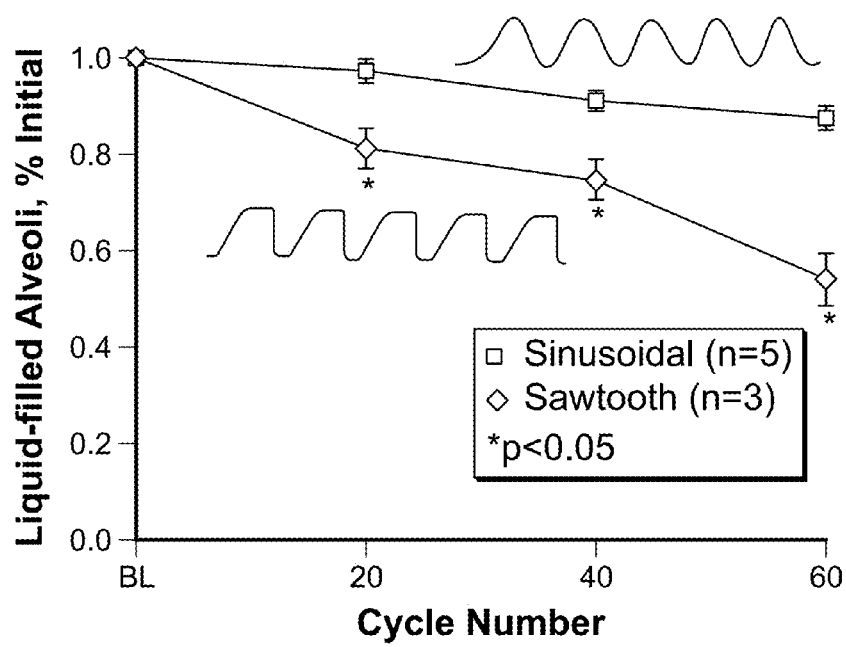
Figure 17C:
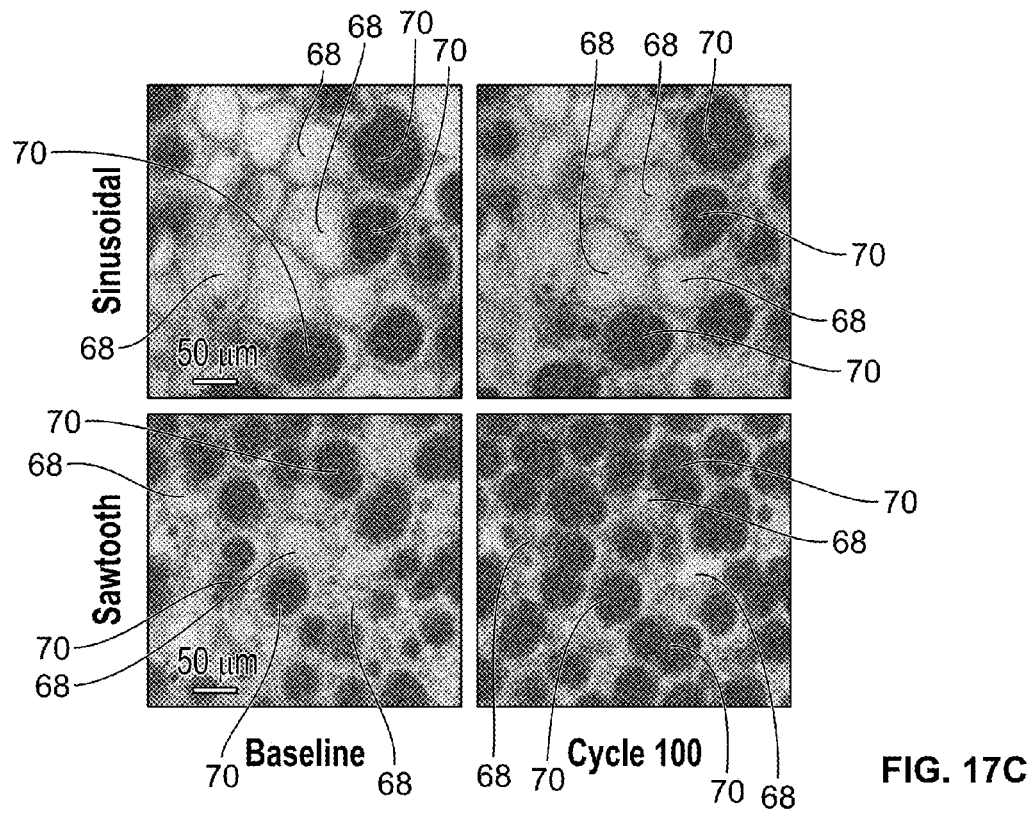
FIGS. 17C and 17D are a pairing of a set of micrographs and a graph comparing clearance of alveoli in a global permeability edema model by ventilation using a sinusoidal pressure waveform and ventilation using a sawtooth waveform, according to embodiments of the present invention.
Figure 17D:
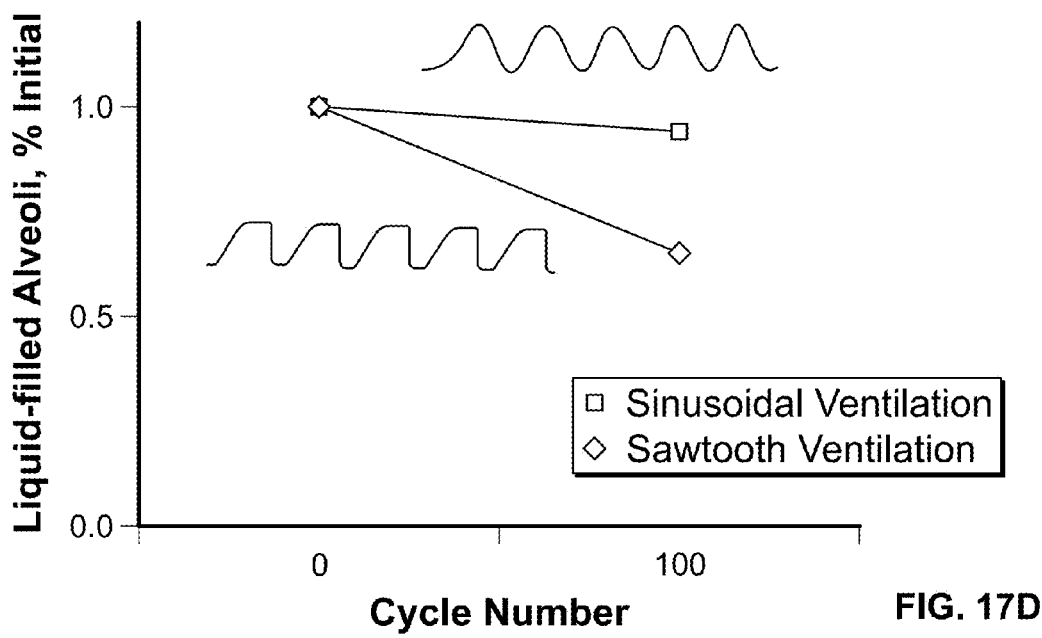

FIGS. 17A and 17B are a pairing of a set of micrographs and a graph comparing clearance of alveoli by ventilation using sinusoidal and sawtooth pressure waveforms, as are FIGS. 17C and 17D. FIGS. 17A and 17B illustrate results obtained ventilating a local edema model, and FIGS. 17C and 17D illustrate results obtained using a global permeability edema model. Both ventilation patterns were used at a cycle frequency of 0.2 Hz between $P_{ALV}$ of 5 and 15 cmH$_2$O. Baseline (BL), indicated on the graph of FIG. 17B, is following 20 cycles of sinusoidal ventilation in each group, to clear unstable alveoli and test the ventilation patterns on stably flooded alveoli. As can be seen from the micrographs and graphs of FIGS. 17A, 17B, 17C, and 17D, ventilation using a sawtooth waveform opens a greater number of alveoli than does ventilation using a sinusoidal waveform, indicating that the abrupt deflation of the sawtooth ventilation clears alveolar liquid more effectively than sinusoidal ventilation. In FIGS. 17A and 17C, exemplary flooded alveoli 68 are indicated by lighter gray areas, and exemplary aerated alveoli 70 are indicated by darker areas.

Figure 18:
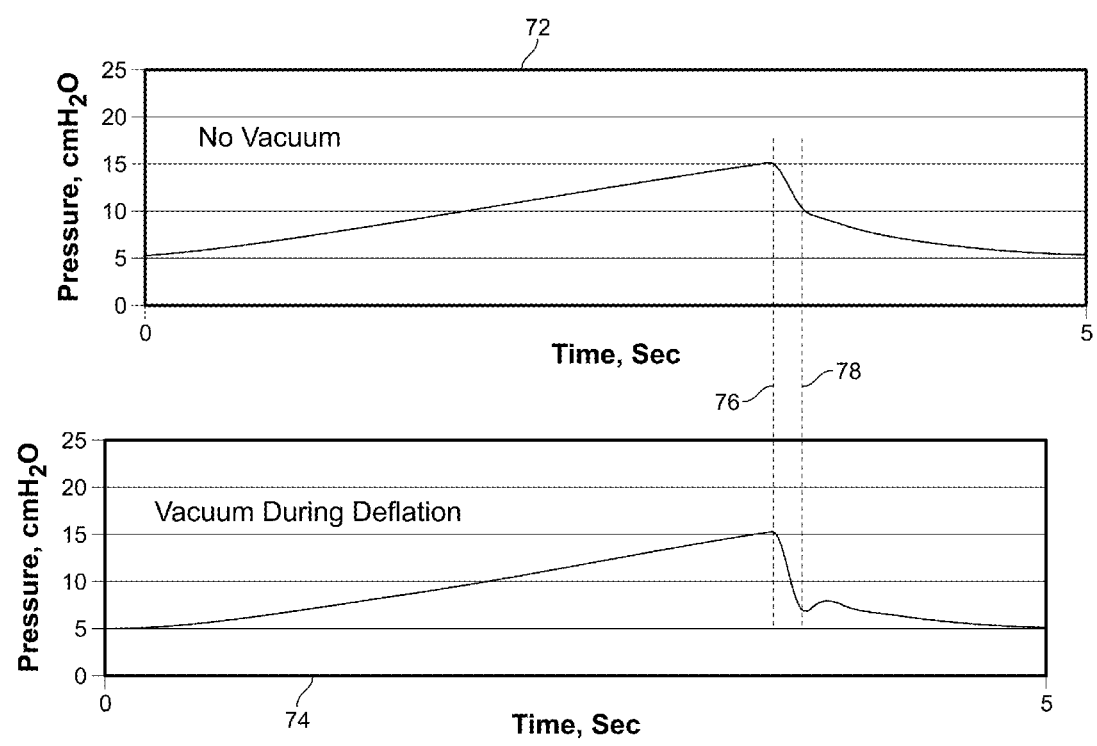
FIG. 18 is a pair of graphs showing the effect of vacuum acceleration during deflation on pressure ventilation waveforms generated according to embodiments of the present invention with the apparatus of FIG. 16.

In some embodiments of the present invention, the lung may be actively deflated at an accelerated rate (accelerated sawtooth), by applying vacuum pressure at gas outlet 54 of the ventilation apparatus 44 shown in FIG. 16 and opening valve 58 suddenly at the start of deflation. Results of this active deflation are shown in the graphs of FIG. 18. The upper graph 72 shows a waveform generated with atmospheric pressure at outlet 54 and sudden opening of valve 58 at the start of deflation. The lower graph 74 shows a waveform generated with vacuum pressure applied at outlet 54 and sudden opening of valve 58 at the start of deflation. The vertical lines 76, 78 indicate the time for the waveform of the upper graph (i.e., the waveform generated without vacuum) to decrease from 15 to 10 cmH$_2$O. As shown in the lower graph, application of vacuum at outlet #2 generates a waveform having a sharper deflation slope, with a shorter time required to decrease pressure from 15 to 10 cmH$_2$O. However, PEEP was maintained (i.e., tracheal pressure never decreased below a set, positive minimal value).

As discussed above with respect to FIGS. 16, 17A, 17B, 17C, 17D, and 18, faster deflation of the lung is effective in clearing liquid from alveoli. Such clearance may be achieved with one or a combination of the following methods, performed according to embodiments of the present invention:

1. Applying vacuum pressure at the exit of the ventilation tubing circuit (e.g., gas outlet 54 in the apparatus of FIG. 16) during deflation; and 2. Stimulating the abdominal and/or intercostal muscles, by functional electrical stimulation, or other means, to generate a cough-like motion synchronized with exhalation/deflation.

Either of the above two methods for causing active deflation, alone or in combination, could be combined with mechanical ventilation; non-invasive ventilation; or lung expansion devices including chest physiotherapy devices and high frequency oscillation devices.

Vacuum may be applied by known means such as vacuum pump, house vacuum line, Venturi tube, reciprocating piston or other mechanism. However, a distinguishing feature of the apparatus of FIG. 16, according to embodiments of the present invention, is the inclusion of a valve on the outlet to vacuum and regulation of that valve in response to pressure measured at the tracheal outlet. Other forms of ventilation with active deflation (HFOV and ventilation with NEEP) apply vacuum pressure in such a manner as to decrease tracheal pressure below atmospheric pressure. Such forms of ventilation do not maintain PEEP. The apparatus of the present invention, by applying vacuum pressure at the exit of the breathing circuit, downstream in the expiratory circuit from the trachea, and terminating vacuum application when tracheal pressure decreases to the desired PEEP level, enables deflation to be actively accelerated while maintaining PEEP in the lung.

3. Vibration or Step or Impulse Force Application to the Lung

Lung motion during breathing is normally smooth. Application of vibration or of step or impulse force to the edematous lungs could perturb surface tension within edematous alveoli in such a fashion as to facilitate equitable edema liquid distribution.

Figure 20A:
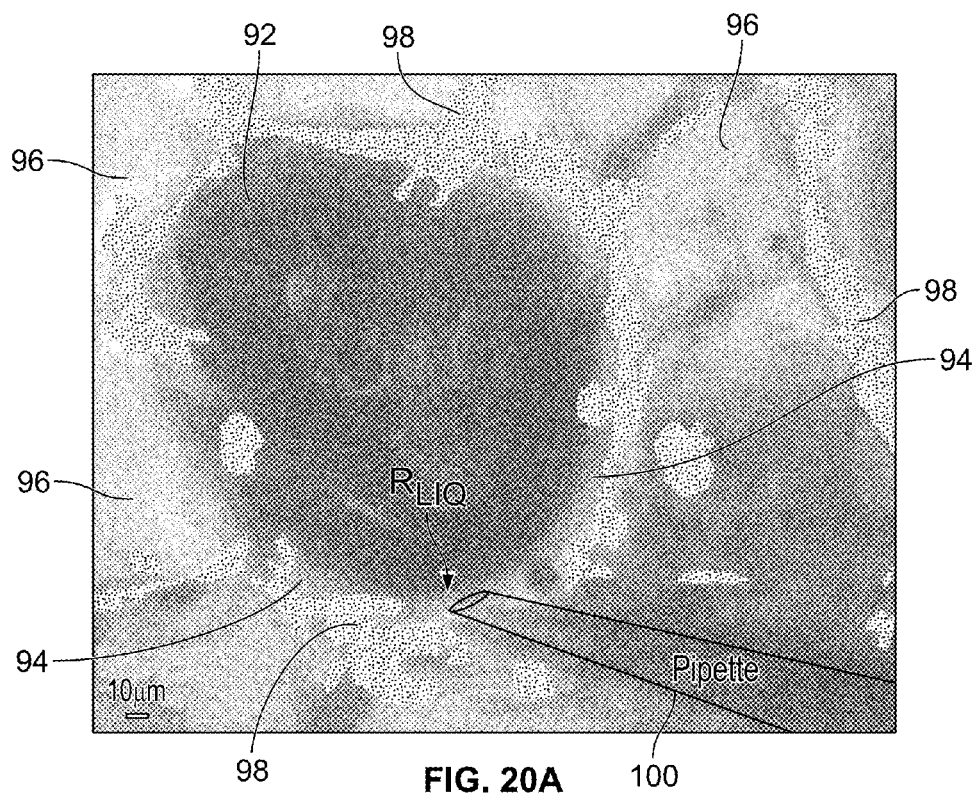
FIGS. 20A and 20B are a pairing of an enhanced micrograph and a graph indicating that surface tension is spatially uniform.
Figure 20B:
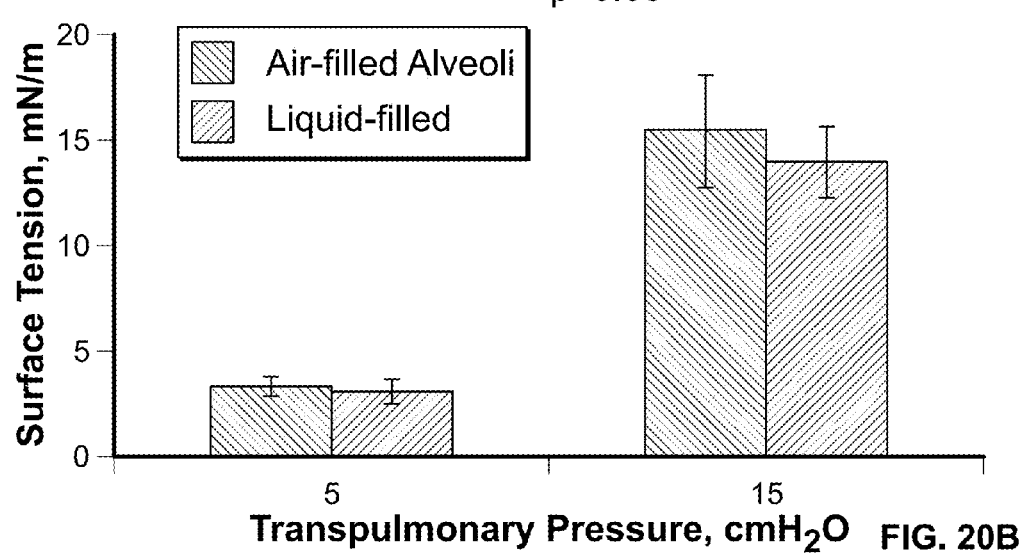

Surface tension is normally spatially uniform in the lung. FIGS. 20A and 20B are a pairing of an enhanced micrograph demonstrating how surface tension is determined in an aerated alveolus and a graph indicating that surface tension is spatially uniform. The micrograph is an image of an aerated alveolus 92, with a liquid lining layer 94, surrounded by edematous alveoli 96. Alveolar walls 98 are indicated by light stippling. The pipette measures the liquid lining layer pressure in the aerated alveolus 92 for surface tension determination according to the Laplace relation. The graph presents grouped surface tension data for adjacent aerated and flooded alveoli (n=3), showing that surface tension does not vary spatially even in a region of heterogeneous alveolar flooding.

Lung vibration could alter the normally uniform surface tension distribution. FIGS. 19C, 19D, and 19E are a group of schematic drawings indicating a conceptual model of vibration effects on edematous alveolar surface tension. Liquid 80 fills the area between the alveolar wall 82 and the air-liquid interface 84. Referring to FIG. 19C, at a normal breathing frequency (0.2 Hz), surfactant distribution and surface tension are constant along the interface 84. Referring to FIG. 19D, a rightward lateral vibration stroke propels the center of the liquid mass 80 to the right because of inertia, and skews the interface 84 to the right such that the interfacial radius R at the right is greater than the radius r at the left. The movement of the liquid 80 compresses the surfactant and lowers surface tension t at the right, and dilates the surfactant and raises the surface tension T at the left, thus generating a tension force to the left. Due to the Laplace relation, liquid pressure $P_{LIQ}$ at the right is greater than pressure $p_{LIQ}$ at the left, thus a net pressure force also acts to the left. Just as interplay between inertia and pressure can cause a resonant "rocking mode" during vibration of a pure water droplet, interplay between inertia, surface tension and pressure has the capacity to generate a "rocking mode" in an edematous alveolus, as depicted in FIG. 19D. Higher frequency vibration, likewise due to the interplay of inertia, surface tension, and pressure, has the potential to generate resonant capillary waves. Referring to FIG. 19E, such resonant capillary waves 86 would compress the surfactant and lower surface tension at the crests 88 of the waves 86 and dilate the surfactant and raise tension at troughs 90 of the waves 86. By the Laplace relation, the pressure below the troughs 90 would be less ($p<P_{ALV}$) than the pressure below the crests 88 ($P>P_{ALV}$).

If surface tension gradients existed along the interface 84, however, they would apply shear stress to, and cause movement of, the liquid 80 below in the interface 84. Thus, vibration of the lung, or application of a step or impulse force to the lung, would generate surface tension gradients at the air-liquid interface 84, and accompanying pressure gradients in the edema liquid 80 below the interface 84. Such induced spatial variation in the surface tension or pressure has the potential to overcome, at random, the pressure barrier trapping liquid in discrete alveoli, therefore to promote clearance of edematous alveoli.

Edematous alveolar liquid pressure is normally maximal at the edge of the alveolus. In the flooded alveolus, liquid pressure $P_{LIQ-BORD}$ at the edge of the alveolus exceeds liquid pressure $P_{LIQ-EDEM}$ in the center of the alveolus (see FIG. 1). Between the two locations, pressure may be assumed to vary smoothly, governed by the smooth variation in interfacial curvature. Perturbation of the normal smooth breathing motion, however, might perturb the typical pattern of pressure variation in edema liquid and cause pressure at the edge of the alveolus transiently to fall below pressure in the center of the alveolus. Referring to FIG. 19A, computational fluid dynamics modeling indicates that such a transient reversal of the pressure barrier is possible. FIGS. 19A and 19B show modeling predictions for effects of lung vibration on edematous alveolar liquid pressure distribution. In the computational fluid dynamic model (Star-CCM+) of FIGS. 19A and 19B, an alveolus is approximated as a 100 micron diameter 3-D sphere with three-quarters of its volume filled with water. Air pressure is modeled at 15 $cmH_2O$. Surface tension is modeled at 15 mN/m, with liquid slipping at the boundary. In FIGS. 19A and 19B, the simulated pressure increases from the darker shading to the lighter shadings. In the simulation, the alveolus was vibrated at 100 Hz, and 45 deg angle. The dashed circles highlight pressure at what would be the border with an adjacent alveolus. Liquid pressure is generally highest at the border, as in FIG. 19A, but sometimes decreases, as in FIG. 19B. Thus, the normal pressure distribution could be inverted independent of any perturbation to interfacial curvature or surface tension. Such a reversal of pressure gradient could, transiently, overcome the pressure barrier $\Delta P_{BARRIER}$ and facilitate clearance of the edematous alveolus.

When vibrating the lung from its periphery, sufficient amplitude is required to overcome damping as the signal propagates. A high frequency signal will travel better through water than air. Thus, the more edematous the lung, the more effective vibration will be as a therapy. In a droplet of pure water as small as an alveolus, the first resonant (rocking) mode would be expected to occur at about 5000 Hz. With the particular geometry of the edematous alveolar interface and inclusion of surfactant at the interface, the resonant frequency is not known, and, in view of the current state of art, is likely to require empirical investigation.

Further, even non-resonant vibration could alter the normal edema liquid pressure distribution in a manner that favor alveolar clearance.

Given the tradeoff between amplitude and frequency, initial tests were performed in the relatively low frequency range of 100-200 Hz. With the local edema model and with the global permeability edema model, vibration of the lung was tested for its ability to clear flooded alveoli. A function generator was used to drive a speaker coil and the speaker cone was placed in contact with the lung surface, separated from the lung surface by saran wrap. As a control, the speaker cone was pressed against the lung surface with the same force as in the test, but in the absence of power to the speaker, such that the speaker cone did not vibrate. As discussed below with relation to FIGS. 21A, 21B, 21C, and 21D, vibration was found to induce equitable alveolar liquid redistribution in both edema models.

Figure 21A:
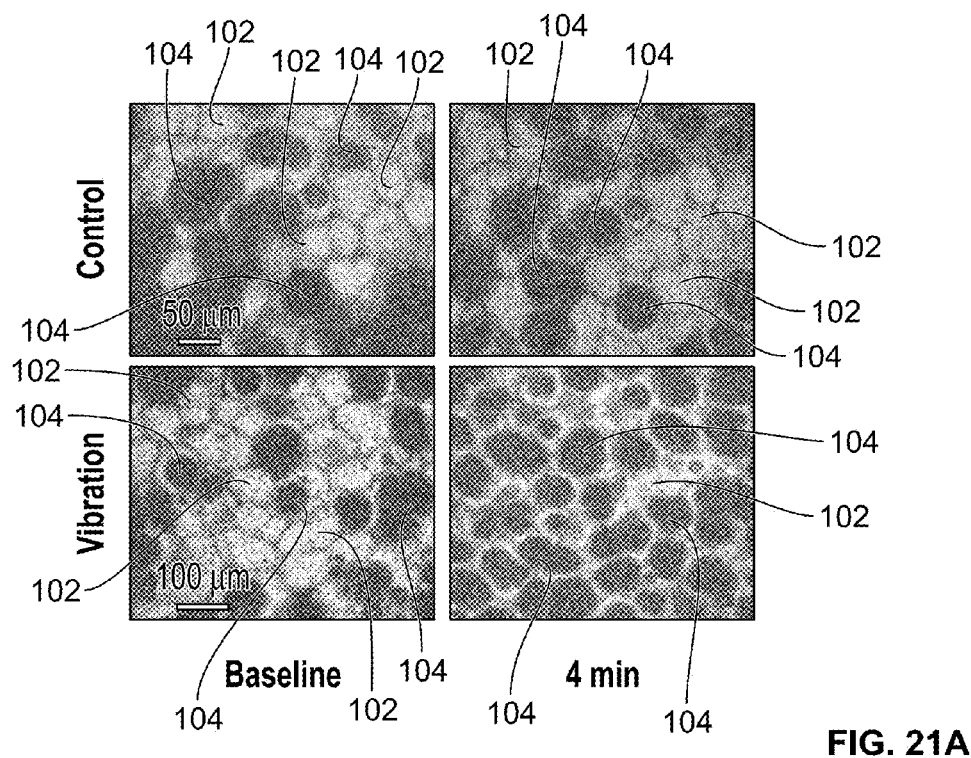
FIGS. 21A and 21B are a pairing of a set of micrographs and a graph illustrating alveolar liquid clearance by vibration of the lung surface in a local edema model according to an embodiment of the present invention.
Figure 21B:
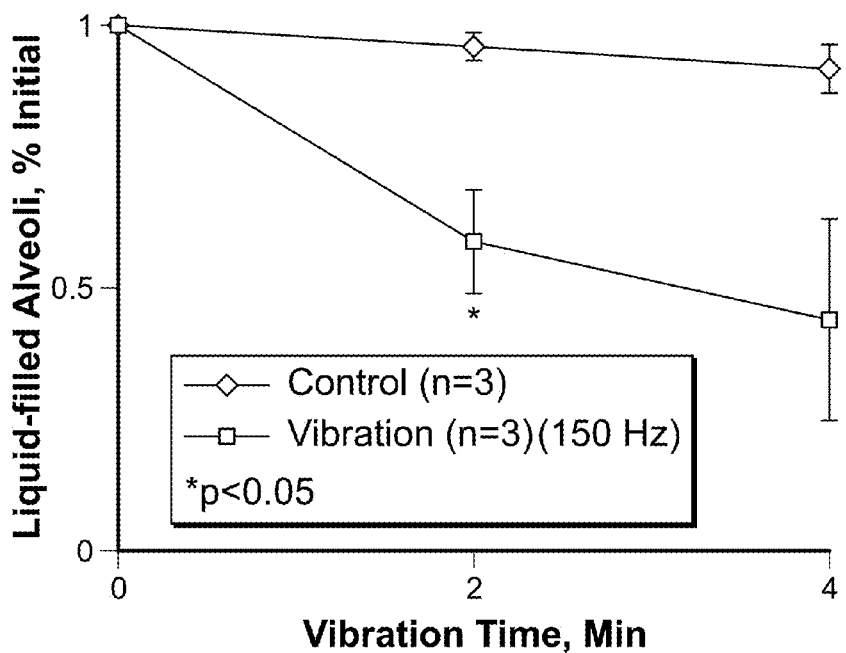
Figure 21C:
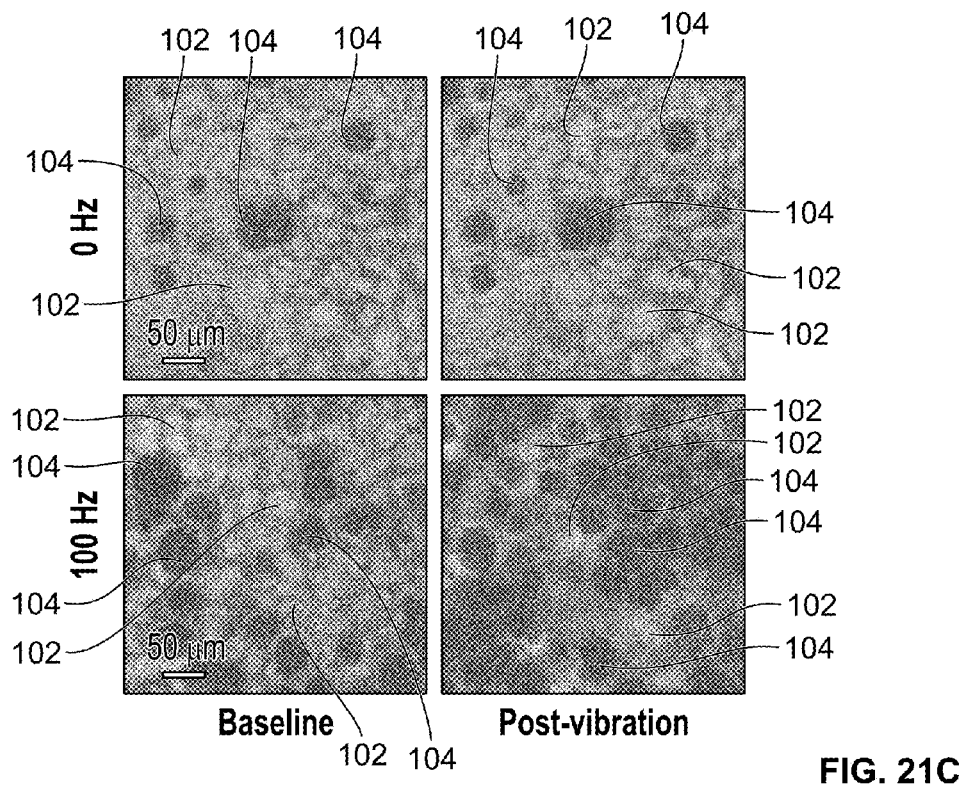
FIGS. 21C and 21D are a pairing of a set of micrographs and a graph illustrating alveolar liquid clearance by vibration of the lung surface in a global permeability edema model according to another embodiment of the present invention.
Figure 21D:
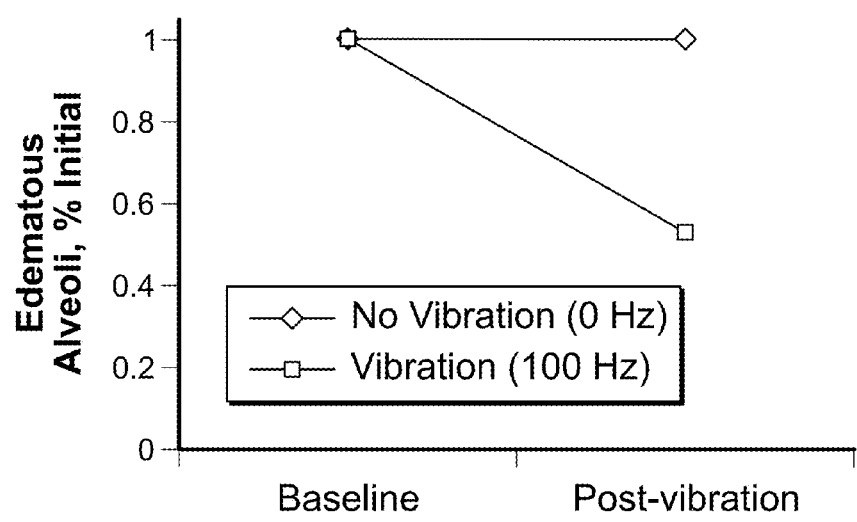

FIGS. 21A and 21B are a pairing of a set of micrographs with a graph indicating that that vibration of the lung surface promotes alveolar liquid clearance, as are FIGS. 21O and 21D. FIGS. 21A and 21B show vibration results in the presence of a local edema model. The alveolar flooding liquid is 5% fatty acid-bound BSA in normal saline with 32 µM BCECF. To clear unstable alveoli, the lung is ventilated with 20 sinusoidal cycles between 5 and 15 cmH$_2$O at 0.2 Hz prior to baseline (cycle 0). The micrographs of FIG. 21A include images of the edematous area at baseline and after four minutes of being pressed against a speaker coil (separated by saran wrap) while speaker is unpowered (control) or vibrating at 150 Hz (vibration). The lung was constantly inflated to P$_{ALV}$ of 15 cmH$_2$O during the experiment. It can be seen that vibration effectively clears the alveoli. FIG. 21B presents the results graphically. FIGS. 21C and 21D present the results of the same experiment as that of FIGS. 21A and 21B, replicated in a global permeability edema model with fluorescein (36 µM) included in the perfusate. The lung was vibrated at 100 Hz for 2 min, while held at constant P$_{ALV}$ of 15 cmH$_2$O. It can be seen that vibration effectively clears the alveoli in this model also. In FIGS. 21A and 21O, flooded alveoli 102 are shown as light or medium gray areas, and aerated alveoli 104 are shown as darker areas 104.

To apply vibrations of ≥50 Hz to the lung for edema liquid redistribution, the following methods could be employed individually, in combination and/or in conjunction with mechanical ventilation; non-invasive ventilation; or lung expansion devices including chest physiotherapy devices and high frequency oscillation devices, according to various embodiments of the present invention:

1. Coupling a speaker coil, oscillator or ultrasound generator to the patient's chest wall or back;
2. Implanting a speaker coil, oscillator or ultrasound generator in the fluid-filled plural space (outside the lungs, inside the ribcage);
3. Inserting a fluid-filled conduit into the pleural space and, via the conduit, hydraulically applying a high frequency pressure signal to the pleural fluid, with, e.g., a speaker coil, oscillator or an ultrasound generator;
4. Coupling a speaker coil, oscillator or ultrasound generator to the trachea, either directly or through the skin;
5. Percussing the chest and/or back with a commercially-available device intended for that purpose (e.g., a pneumatic vest); and
6. Adding a ≥50 Hz component to an existing ventilation pressure, volume or flow waveform.

In some embodiments of the invention, a step or impulse force could be applied to the lung, rather than a vibration. In ideal form, step and impulse functions are of infinite frequency. The actual frequency of force application to the lung would not be infinite, but would be maximal. Thus, repetitive application of a step or impulse force to the lung would promote edematous alveolar clearance. A step or impulse function would be employed alone or in conjunction with mechanical ventilation; non-invasive ventilation; or lung expansion devices including chest physiotherapy devices and high frequency oscillation devices, by one of the following methods:

1. Any of the mechanisms discussed above with respect to vibration of the lung at high frequency;
2. Any of the mechanisms for sudden deflation discussed in Section 2; and
3. Transient airway occlusion during deflation, particularly in combination with active, accelerated deflation. Transient airway occlusion could be effected with transient closure of a valve at airway exit; a spinning ball or high frequency flow interrupter, such as are used in high frequency percussive ventilation; or other mechanism. Deflation could be accelerated by any of the mechanisms discussed in Section 2; by use of a Hayek Oscillator; or by other means.

It will be understood that the embodiments described herein are merely exemplary and that a person skilled in the art may make many variations and modifications without departing from the spirit and scope of the invention. All such variations and modifications are intended to be included within the scope of the invention described in the claims appended hereto.

I claim:

1. A method of relieving ventilation injury of a lung containing regions with heterogeneous alveolar flooding by alveolar liquid, comprising the step of delivering to the alveolar liquid at least one rhodamine dye, thereby increasing the concentration of the at least one rhodamine dye to a concentration that is greater than about 0.1 nM and less than about 1 µM or greater than about 1 µM and less than about 10 µM, thereby lowering the surface tension of the alveolar liquid so as to lessen ventilation injury.

2. The method of claim 1, wherein the alveolar liquid includes albumin in the range of greater than about 1.8% to about 12% during said delivering step.

3. The method of claim 1, wherein the alveolar liquid includes albumin in the range of about 3% to about 5% during said delivering step.

4. The method of claim 1, wherein the alveolar liquid includes albumin in a concentration of about 5% during said delivering step.

5. The method of claim 1, wherein the alveolar liquid includes albumin in a concentration of about 3% during said delivering step.

6. The method of claim 1, wherein said delivering step is performed so as to increase the concentration of the at least one rhodamine dye in the alveolar liquid to the range of about 1 nM to about 100 nM.

7. The method of claim 1, wherein said delivering step is performed so as to increase the concentration of the at least one rhodamine dye in the alveolar liquid to the range of about 10 nM to about 100 nM.

8. The method of claim 1, wherein said delivering step is performed so as to increase the concentration of the at least one rhodamine dye in the alveolar liquid to the range of about 1 nM to about 10 nM.

9. The method of claim 1, wherein the rhodamine dye includes at least one of sulforhodamine B or rhodamine WT.

10. The method of claim 1, wherein said delivering step is performed such that the concentration of albumin in the alveolar liquid is within the range of greater than about 1.8% to about 12%.

11. The method of claim 1, wherein said delivering step is performed such that the concentration of albumin in the alveolar liquid is at a concentration in the range of about 3% to about 5%.

12. The method of claim 1, wherein said delivering step is performed such that the concentration of albumin in the alveolar liquid is at about 5%.

13. The method of claim 1, wherein said delivering step is performed such that the concentration of albumin in the alveolar liquid is at about 3%.

14. The method of claim 1, wherein said delivering step is performed such that the concentration of the at least one rhodamine dye in the alveolar liquid is in the range of about 1 nM to about 100 nM and the concentration of albumin in the alveolar liquid is in the range of about 3% to about 5%.

15. The method of claim 1, wherein said delivering step is performed such that the concentration of the at least one rhodamine dye in the alveolar liquid is in the range of about 1 nM to about 10 nM and the concentration of albumin in the alveolar liquid is in the range of about 3% to about 5%.

16. The method of claim 1, wherein said delivering step includes the further step of delivering albumin to the alveolar liquid.

17. The method of claim 16, wherein the albumin includes a serum albumin.

18. The method of claim 1, wherein said delivering step is performed such that the lowered surface tension of the alveolar liquid lessens ventilation-induced over-expansion injury of aerated alveoli located adjacent to flooded alveoli.

19. The method of claim 1, wherein said delivering step includes the step of administering a solution containing one or both of the at least one rhodamine dye and the albumin to the trachea or bronchi of a patient having regions with heterogeneous alveolar flooding by alveolar liquid in a lung.

20. The method claim 19, including the further step of administering a solution containing a surfactant to the trachea or bronchi of the patient.

21. The method of claim 19, wherein the solution further includes a surfactant.

22. The method of claim 1, wherein said delivering step includes the step of administering a solution containing the at least one rhodamine dye by injecting the solution into the circulatory system of a patient having the lung containing regions with heterogeneous alveolar flooding by alveolar liquid.

23. The method of claim 22, wherein the solution includes albumin.

24. The method of claim 1, wherein said delivering step is performed so as to increase the concentration of the at least one rhodamine dye in the alveolar liquid to the range of about 1 nM to less than about 1 μM.

25. The method of claim 1, wherein said delivering step is performed so as to increase the concentration of the at least one rhodamine dye in the alveolar liquid to the range of about 10 nM to less than about 1 μM.

\* \* \* \* \*

UNITED STATES PATENT AND TRADEMARK OFFICE
CERTIFICATE OF CORRECTION

PATENT NO. : 9,693,990 B2
APPLICATION NO. : 14/940675
DATED : July 4, 2017
INVENTOR(S) : Carrie E. Perlman Page 1 of 1

It is certified that error appears in the above-identified patent and that said Letters Patent is hereby corrected as shown below:

In the Specification

Column 1, before the first paragraph on Line 4, insert the following:
-- Statement Regarding Federally Sponsored Research
This invention was made with government support under Grant Number HL113577 awarded by The National Institutes of Health. The government has certain rights in the invention. --

Signed and Sealed this
Fifteenth Day of September, 2020

Andrei Iancu
*Director of the United States Patent and Trademark Office*